(12) United States Patent
Kwok et al.

(10) Patent No.: US 10,946,099 B2
(45) Date of Patent: Mar. 16, 2021

(54) COMPOSITIONS FOR PHOTODYNAMIC THERAPY AND FLUORESCENCE DIAGNOSIS OF CANCERS AND OTHER DISEASES

(71) Applicant: VISION GLOBAL HOLDINGS LIMITED, Kowloon (HK)

(72) Inventors: Sui Yi Kwok, Kowloon Bay (HK); Norman Fung Man Wai, Vancouver (CA); Terence Shau Yin Wai, Richmond (CA); Shan Yu, Kowloon Bay (HK)

(73) Assignee: VISION GLOBAL HOLDINGS LIMITED, Kowloon (HK)

( * ) Notice: Subject to any disclaimer, the term of this patent is extended or adjusted under 35 U.S.C. 154(b) by 0 days.

(21) Appl. No.: 16/020,334

(22) Filed: Jun. 27, 2018

(65) Prior Publication Data
US 2019/0054173 A1 Feb. 21, 2019

Related U.S. Application Data

(60) Provisional application No. 62/525,471, filed on Jun. 27, 2017.

(51) Int. Cl.
*A61K 41/00* (2020.01)
*A61P 35/00* (2006.01)
*A61K 47/64* (2017.01)

(52) U.S. Cl.
CPC .......... *A61K 41/0071* (2013.01); *A61K 47/64* (2017.08); *A61P 35/00* (2018.01)

(58) Field of Classification Search
None
See application file for complete search history.

(56) References Cited

U.S. PATENT DOCUMENTS

2006/0067889 A1 3/2006 Pallenberg et al.
2016/0000864 A1* 1/2016 Wong ................. A61K 38/1709
514/1.2

FOREIGN PATENT DOCUMENTS

| CN | 1874789 A | 12/2006 |
| CN | 103330938 A | 10/2013 |
| CN | 104940950 A | 9/2015 |
| CN | 105481946 A | 4/2016 |
| WO | 2007023398 A2 | 3/2007 |
| WO | 2008130181 A1 | 10/2008 |

OTHER PUBLICATIONS

J. Fyrestam, et al., "Determination of Porphyrins in Oral Bacteria by Liquid Chromatography Electrospray Ionization Tandem Mass Spectrometry," Anal Bioanal Chem (2015) 407:7013-7023.
International Search Report dated Oct. 25, 2018, corresponding to PCT/IB2018/054774.

* cited by examiner

*Primary Examiner* — Iqbal H Chowdhury
(74) *Attorney, Agent, or Firm* — Hogan Lovells US LLP

(57) ABSTRACT

The invention relates to pharmaceutical compositions comprising a conjugate of a porphyrin (e.g., PpIX) and a recombinant protein. The pharmaceutical compositions of the invention may be used in photodynamic therapy. The invention also relates to methods of producing such pharmaceutical compositions and to methods of using such pharmaceutical compositions in the treatment of diseases, such as cancer.

13 Claims, 17 Drawing Sheets
(12 of 17 Drawing Sheet(s) Filed in Color)
Specification includes a Sequence Listing.

PpIX-TF conjugate is named as TF01

(A)

(B)

★ 5 mg/ml TF01(batch 1) approximately contains 53uM PpIX.

COMPOSITIONS FOR PHOTODYNAMIC THERAPY AND FLUORESCENCE DIAGNOSIS OF CANCERS AND OTHER DISEASES

RELATED APPLICATIONS

This application claims priority to US provisional application 62/525,471 filed on Jun. 27, 2017, the contents of which are incorporated by reference in their entirety.

SEQUENCE LISTING

The instant application contains a Sequence Listing which has been filed electronically in ASCII format and is hereby incorporated by reference in its entirety. Said ASCII copy, created on Sep. 11, 2018, is named 046217-000010_SL.txt and is 56,220 bytes in size.

FIELD OF THE INVENTION

The invention relates to pharmaceutical compositions comprising a conjugate of protoporphyrin LX and a recombinant protein, wherein the conjugate comprises high levels of protoporphyrin IX. The invention also relates to methods of producing such pharmaceutical compositions and to methods of using such pharmaceutical compositions in the treatment of diseases, such as cancer.

BACKGROUND OF THE INVENTION

Photodynamic therapy (PDT) is a therapeutic strategy and treatment procedure that uses a photosensitizer to produce reactive oxygen species in order to kill malignant cells or other disease cells. PDT can be used to treat cancers (including bladder, cervical, esophageal, gastric, lung and skin cancers) and also non-malignant diseases (including acne, macular degeneration and psoriasis). In PDT, upon exposure to irradiating light (at a wavelength appropriate for the photosensitizers), the photosensitizers are excited from the ground state ($S_0$) to the first singlet state (Si) and then the longer lived triplet state ($T_1$) via an intersystem crossing system. After excitation, the photosensitizers return to the ground state ($S_0$) from the triplet state ($T_1$), resulting in an emission of light (fluorescence) or transferring of energy to another particle or system (radiation-less transition). In the latter transition process (radiation-less transition), many reactive oxygen species are produced (ROS; including singlet oxygen/$^1O_2$, hydrogen peroxide/$H_2O_2$, and superoxide radicals/$O_2^-$), which can kill tumor cells by directly damaging them as well as by destroying the tumor vasculature. Among these ROS, $^1O_2$ is the active predominant cytotoxic agent in PDT. PDT is also an ideal therapeutic procedure for cancer treatment because it is clinically approved and minimally invasive.

Protoporphyrin IX (PpIX; 7,12-diethenyl 3,8,13,17-tetramethyl-2111,2311-porphine 2,18-dipropanoic acid) has been utilized as a photosensitizer in both PDT and photodynamic diagnosis (PDD). PpIX is a metal-free porphyrin that is the direct precursor of heme. The biological heme biosynthesis pathway is a conservative process among prokaryotes (e.g., bacteria) and eukaryotes (including humans). Ferrochelatase is the terminal enzyme in the heme biosynthesis and is responsible for the enzymatic insertion of $Fe^{2+}$ into PpIX.

There are issues with both direct and indirect application of PpIX in PDT. For example, direct topical application of PpIX can induce increased levels of PpIX in tumor tissues. However, PpIX has some intrinsic problems, particularly its high hydrophobicity and low solubility in aqueous solutions. Its low solubility in water can cause accumulation in the skin, resulting in prolonged photosensitivity up to several weeks after PDT treatment. For systematic application of PpIX, its poor localization or targeting of cancer cells also limits its direct application for PDT.

An alternative approach to direct topical application of PpIX is indirect application of PpIX by mediation with 5-aminolevulinic (5-ALA), the precursor of PpIX biosynthesis, a treatment called "ALA-PDT." In this procedure, 5-ALA is administered and enters the heme biosynthesis pathway in the cancer cells and then stimulates the PpIX synthesis that causes PpIX accumulation. Upon excitation with light irradiation, the cancer cells are eradicated. However, the accumulation of PpIX in cancer cells may vary in different cancer types that depend on the cellular concentration of ALA, the activity of enzymes involved and some other cellular factors. Thus, the therapeutic application of ALA-PDT is limited with respect to some cancer types because it is difficult to achieve high levels of PpIX accumulation. During the past years, many efforts have been made to improve the ALA-PDT treatment procedure, by modifying or conjugating ALA to carriers and taken up by target cancer cells. However, these kinds of modification or conjugation are complicated and very expensive which also limit the therapeutic applications.

In view of these limitations, it would be advantageous to develop a method of enabling the selective accumulation or up-take of photosensitizers, such as PpIX, in the target cells relative to the surrounding non-target tissues in order to enhance the effective treatment of the diseased tissues while reducing the collateral side effects.

SUMMARY OF THE INVENTION

In one aspect, the invention provides a pharmaceutical composition comprising an effective amount of at least one type of conjugate comprising a porphyrin and a recombinant protein, and a pharmaceutically acceptable excipient. The porphyrin and the recombinant protein may be, for example, PpIX and TF (globin $2\alpha\beta2$ tetramer). The conjugate of PpIX and TF is referred to herein as TF01.

In another aspect, the invention provides a method of treating cancer. The method includes administering an effective amount of a pharmaceutical composition to an area of a patient in need of treatment. The pharmaceutical composition comprises at least one type of conjugate comprising a porphyrin and a recombinant protein, and a pharmaceutically acceptable excipient. The method further includes irradiating the area in need of treatment to generate reactive oxygen species after administration of the pharmaceutical composition, thereby treating the cancer.

In another aspect, the invention provides a method of reducing the volume of a tumor in a subject. The method includes administering an effective amount of a pharmaceutical composition to an area of the subject where the tumor is found. The pharmaceutical composition comprises at least one type of conjugate comprising a porphyrin and a recombinant protein, and a pharmaceutically acceptable excipient. The method further includes irradiating the area in which the tumor can be found to generate reactive oxygen species after administration of the pharmaceutical composition, thereby reducing the volume of the tumor in the area of the subject where the tumor is found.

In yet another aspect, the invention provides a method of producing a pharmaceutical composition. The method comprises constructing a vector plasmid comprising a promoter, a recombinant protein, and a selectable marker. The vector plasmid transforms a bacterial strain by inserting the plasmid therein. The bacterial strain is one that endogenously produces PpIX. The method further comprises selecting bacterial clones using an antibiotic corresponding to the selectable marker and culturing the bacterial clones in a fermentation medium. The method also includes the step of purifying conjugates from the fermentation medium, wherein the conjugates comprise PpIX non-covalently associated with the recombinant protein. Optionally, a pharmaceutically acceptable carrier may be added to the purified conjugates, thereby forming the pharmaceutical composition.

BRIEF DESCRIPTION OF THE DRAWINGS

The file of this disclosure contains at least one drawing executed in color. Copies of this patent with color drawing(s) will be provided by the Patent and Trademark Office upon request and payment of the necessary fee. Some embodiments of the disclosure may be understood by referring, in part, to the present disclosure and the accompanying drawings.

FIG. 8.

DETAILED DESCRIPTION OF THE INVENTION

The patent or application file contains at least one drawing executed in color. Copies of this patent or patent application publication with color drawing(s) will be provided by the Office upon request and payment of the necessary fee.

In one aspect, the invention provides a pharmaceutical composition comprising a conjugate that comprises a porphyrin (e.g., PpIX) and a protein. The pharmaceutical compositions of the invention are useful for a variety of different purposes, including the treatment of cancer in connection with photodynamic therapy. The invention recognizes that the conjugate comprising protein bound to the porphyrin acts as a carrier for the porphyrin, preventing the self-aggregation of the porphyrin and the improvement of the porphyrin's properties including water solubility, dispensability, fluorescence, and generation of reactive oxygen species. This invention also recognizes that conjugates comprising porphyrin and a protein, as described herein, will undergo enhanced uptake by target cells, including cancer cells. Accordingly, the invention recognizes that the pharmaceutical compositions of the invention will exert enhanced photo-damage on targeted cancer cells when applied in connection with photodynamic therapy. In addition, the invention recognizes that the PpIX-protein conjugates described herein minimize undesirable side effects commonly associated with application of unconjugated PpIX in photodynamic therapy.

Figure 1:
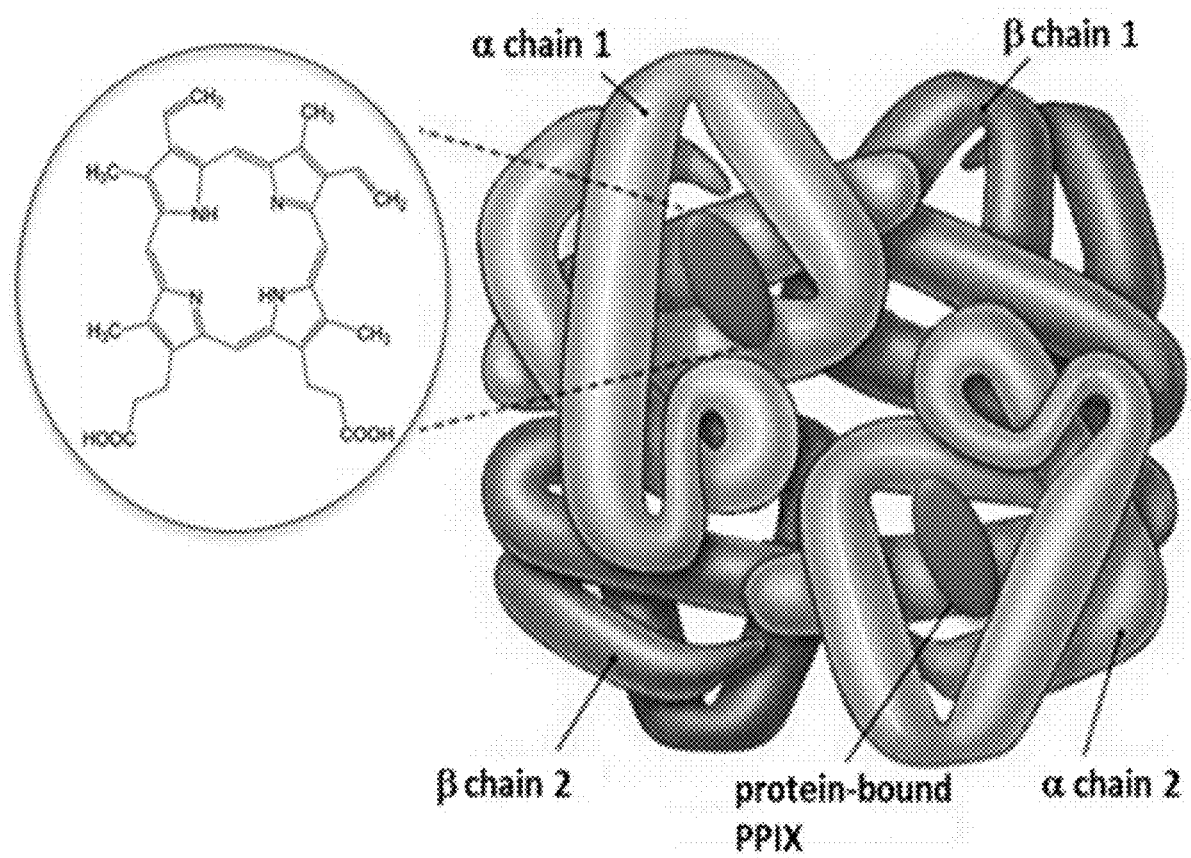
FIG. 1: A schematic diagram of the PpIX bound to the recombinant protein (in this case, TF (human globin 2α and β chain sequences, present as a 2αβ2 tetramer).

In preferred embodiments of the invention, the pharmaceutical compositions contain a conjugate comprising PpIX and a protein, as described herein. It is to be understood, however, the invention also contemplates the use of other porphyrins, instead of or in addition to PpIX, that are capable of generating therapeutic reactive oxygen species upon irradiation with electromagnetic radiation of the appropriate wavelength. Non-limiting examples of such porphyrins include modified protoporphyrin IX, meta tetrahydroxyphenyl chlorin (mTHPC), benzoporphyrin derivative (BPD) and metal binding protoporphyrins, such as zinc protoporphyrin. In general, the conjugates of the invention may be formed by combining a porphyrin, such as PpIX, with a protein capable of binding with the porphyrin, such as, for example any protein known to bind non-covalently with heme. Without wishing to be limited by theory, it is believed that the porphyrin (e.g., PpIX) is non-covalently associated with the protein in the conjugate, as evidenced by the observation that PpIX can be isolated from conjugates of the invention by extraction with HCl-acetone. In this context, the term "non-covalently associated" refers to binding that does not result from the formation of one or more covalent bonds between the porphyrin and the protein, but rather from intermolecular forces such as hydrogen bonding, London forces, dipole-dipole interactions, and the like. A schematic illustration of such a non-covalently associated conjugate is provided in FIG. 1. As shown in FIG. 1, the PpIX-TF conjugate (referred to herein as TF01) comprises a protein with one di-alpha chain and two beta chains, with which PpIX molecules (here two for the purposes of illustration) are non-covalently associated. In certain embodiments, the porphyrin and the protein are obtained separately and physically combined to form the conjugate. For example, the protein may be recovered from natural sources or produced recombinantly and then combined with the porphyrin. In other embodiments, the porphyrin and protein are produced together. For example, when the porphyrin is PpIX, the invention contemplates producing the protein recombinantly in bacteria that naturally produce PpIX. Bacteria that naturally produce PpIX have been reported, for example, by Fyrestam et al. See Fyrestam, J., Bjurshammar, N., Paulsson, E. et al. Anal. Bioanal. Chem. (2015) 407:7013. The invention recognizes that PpIX naturally binds via non-covalent association to proteins when the proteins (e.g., globular proteins) are expressed in certain types of bacteria. In this way, the PpIX-protein conjugate can be produced cost-effectively and efficiently by using suitable fermentation and purification techniques, as described herein.

The proteins that are used in the conjugates of the invention are not particularly limited and can be any protein that does not cause any adverse biological effect on a patient and that is capable of non-covalently associating with PpIX or other porphyrins to form a therapeutically useful conjugate for photodynamic therapy. In certain preferred embodiments, the protein is a globular protein. Non-limiting examples of suitable proteins include TF (Globin 2αβ2 tetramer) (SEQ ID NO: 1 and 2), myoglobin (SEQ ID NO: 3), cytochrome P450 (SEQ ID NO: 4), cytochrome C (SEQ ID NO: 5), nitric oxide (NO) synthase (isoform 1, SEQ ID NO: 6, isoform 2, SEQ ID NO: 7, isoform 3, SEQ ID: NO. 8), Rev-erbα (SEQ ID NO: 9) and Rev-erbβ (SEQ ID NO: 10). As noted previously, the protein may be produced recombinantly in bacterial strains that naturally produce PpIX, so that the PpIX-protein conjugate can be recovered efficiently. Some examples of useful bacterial strains include, without limitation, the Jm109(DE3), clear coli, and BL21(DE3) strains of E. coli. In one particularly useful embodiment, the recombinant protein is TF and a PpIX-TF conjugate (TF01) is formed as described herein. Generally, the native human sequences may be used in the methods of the invention described herein. In some embodiments, fragments or subunits of di-alpha chains or beta chains or gamma chains of globins may be used as the recombinant protein. In a preferred embodiment, the recombinant protein is TF and contains one di-alpha chain (~32 kDa) and two beta chains (~16 kDa for each chain).

Suitable conjugates of the invention include those in which the porphyrin-protein molar ratio is the range of about 0.05 to about 4.00, or about 0.10 to about 2.00, or about 0.5 to about 1.0, with the understanding that the end points of each of these ranges may be combined to form additional sub-ranges that are within the scope of the invention. In some embodiments, the porphyrin and the protein are prepared separately and then combined together to form the therapeutic conjugates of the invention. For example, when the porphyrin is PpIX and the protein is TF, the PpIX may be isolated from bacterial sources and the TF may be isolated from serum-derived sources or recombinantly and then combined together to form a PpIX-TF conjugate (TF01) with a suitable molar ratio of PpIX to TF. In certain preferred embodiments, however, the porphyrin-protein conjugates are obtained from a bacterial strain that is capable of producing both the desired porphyrin and protein. For example, a PpIX-TF conjugate (TF01) may be produced by recombinantly expressing TF in bacterial strains that also produce PpIX. In such cases, substantially amounts of the PpIX-TF conjugates (TF01) may be recovered efficiently by suitable fermentation and recovery steps as described herein. When PpIX-TF conjugates are formed in this manner, useful PpIX-TF molar ratios are typically in the range of about 0.05 to about 4.

The invention also provides pharmaceutical compositions comprising porphyrin-protein conjugates of the invention. In certain preferred embodiments, the pharmaceutical compositions comprise only one type of conjugate (e.g., PpIX-TF), but the invention also contemplates adding two or more different types of conjugates when producing pharmaceutical compositions. Preferably, the conjugates are present in the pharmaceutical compositions in an effective amount. As used herein, the term "effective amount" refers to an amount that is implicitly safe, but sufficient to provide a therapeutic benefit to a patient in connection with photodynamic therapy. In addition to the one or more types of conjugates, the pharmaceutical compositions may also include a pharmaceutically acceptable carrier. Non-limiting examples of pharmaceutically acceptable carriers include solvents (e.g., buffered saline), bulking agents, viscosity modifying agents, surfactants, dispersing agents, isotonic agents, coatings, release control agents, and the like.

The pharmaceutical compositions of the invention may be administered to a patient in a variety of different ways including intravenous, intratumoral, intraperitoneal, or even subcutaneous injection, to name just a few. In certain embodiments, the pharmaceutical compositions are applied topically to the area in need of treatment prior to irradiation by light of an appropriate wavelength to generate reactive oxygen species. In such embodiments, it is sometimes useful to include viscosity modifying agents in the pharmaceutical composition to help the pharmaceutical composition remain localized after topical application. Alternatively, the pharmaceutical compositions may be directly injected into an area in need of treatment. The light that interacts with the pharmaceutical compositions of the invention to generate the reactive oxygen species may be supplied directly to the application area by irradiating the skin with an external light source or by delivering the light via a surgically inserted fiber optic cable, depending on the depth of administration and the wavelength of light used. In certain preferred embodiments, the light has a wavelength in the range of 300 nm to 700 nm. For example, when the porphyrin-protein conjugate is PpIX-TF (TF01), it is advantageous to use light with a wavelength of 630 nm. Examples of suitable light sources include lasers (e.g., those with an output wavelength in within the visible/UV spectrum) as well as non-coherent light sources. Non-limiting examples of useful light intensities include those in the range of about 20 $J/cm^2$ to about 200 $J/cm^2$.

Using the pharmaceutical compositions and methods disclosed herein, one can treat a variety of different cancers and other diseases. Non-limiting examples of cancers that may be treated include bladder, cervical, esophageal, gastric, lung and skin cancers. Typically, treatment involves administering the pharmaceutical compositions of the invention to the area in need of treatment (e.g., a tumor) and irradiating with an appropriate wavelength of light to generate reactive oxygen species that have a cytotoxic effect on the cancer cells. The pharmaceutical compositions of the invention may also be used for treating any other disease (e.g., acne) that can be treated using photodynamic therapy. Furthermore, because the pharmaceutical compositions of the invention are readily taken up by cancer cells, they can be used in connection with a fluorescence diagnosis to map the size and shape of a tumor.

Figure 2:
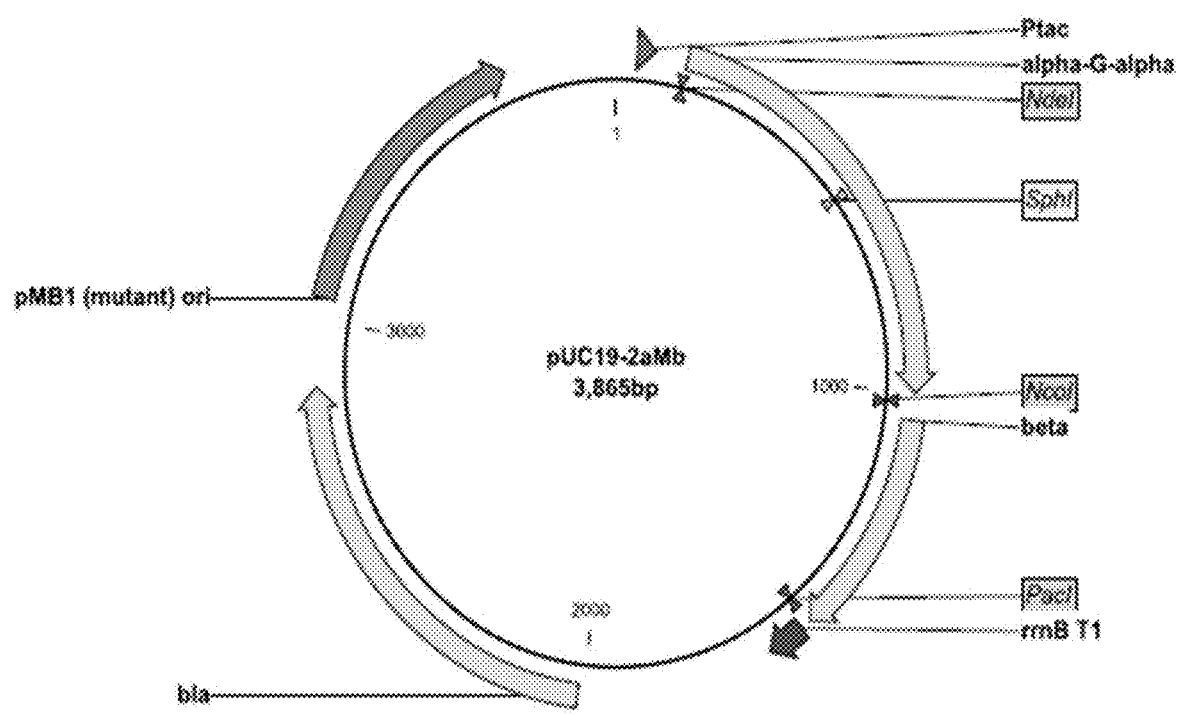
FIG. 2: A vector plasmid comprising sequences for a Ptac promoter, the human globin 2α and β chains of TF, and a selection marker, prepared in accordance with one exemplary embodiment of the invention.

The invention also provides a method of producing porphyrin-protein conjugates recombinantly in high yield. The method comprises inserting sequences for the recombinant protein, a promoter, and a selectable marker into a cloning vector to generate a plasmid vector. Non-limiting examples of suitable cloning vectors include, for example, pUC-19, pBR322, pET, pUC, and so on. Furthermore, non-limiting examples of suitable promoters include Ptac, T7, T7lac, pL, Lac, and so on. For example, when the desired recombinant protein is TF, a useful plasmid vector may be formed by inserting the sequences for a Ptac promoter, the human globin 2α and β chains of TF, and beta-lactamase into a pUC19 to generate a pUC19-24 plasmid, as illustrated in FIG. 2. The vector plasmid is transformed into the bacterial strain. In certain embodiments of the invention, the plasmid is transformed into a bacterial strain and grown overnight at a temperature in the range of 15-40° C., preferably about 37° C. Appropriate bacterial clones are identified using the selectable marker. For example, when the selectable marker causes the expression of beta-lactamase, bacterial clones can be identified using a beta-lactam antibiotic, such as ampicillin.

After appropriate bacterial clones are selected, the bacterial clones are mass produced. In one embodiment, mass production of the bacterial clones is achieved using a two-step fermentation process. In the first step, a seed culture medium is inoculated with the selected bacterial clones. In general, the seed culture medium is not particularly limited and can be any culture medium typically used for production of recombinant proteins by fermentation. For example, in certain embodiments, the culture medium comprises yeast extract and a particularly useful seed culture medium comprises yeast extract (6%) and NaCl (1%). In the second step, after a suitable fermentation period, the seed culture may be added to another culture medium. This second culture medium also is not particularly limited and may comprise ingredients that are typically used for large scale production of recombinant proteins by fermentation. In one exemplary embodiment, the culture medium comprises yeast extract 1%, tryptone 1.6%, $K_2HPO_4$ 14.7 mM, $KH_2PO_4$ 37 mM, NaCl 15.1 mM, $(NH_4)_2SO_4$ 15.14 mM, L-proline 1.998 mM, and glycerol 2%. In addition, while the protein sources in the culture media for producing the recombinant proteins may be derived from animal sources, the invention also contemplates embodiments in which all of the protein sources are "animal-free" (i.e., not derived from any animal products). Non-limiting examples of such protein sources include hydrolyzed soy (e.g., soy peptone), yeast extract, and corn steep liquor. Such embodiments are useful for avoiding issues relating to prion contamination, which can lead to Creutzfeld-Jakob disease. In certain embodiments, fermentation during the second step of the two-step fermentation process continues until the $OD_{600}$ reaches a value in the range of 10-50, preferably 20-45, and even more preferably 30-40. In certain preferred embodiments, the second step of the two-step fermentation process may contain two or more phases. For example, as described herein, the second step of the two-step fermentation process may include an aerobic phase, followed by an induction phase in which isopropyl-β-d-thiogalactoside (IPTG) is added to induce protein expression.

Figure 3:
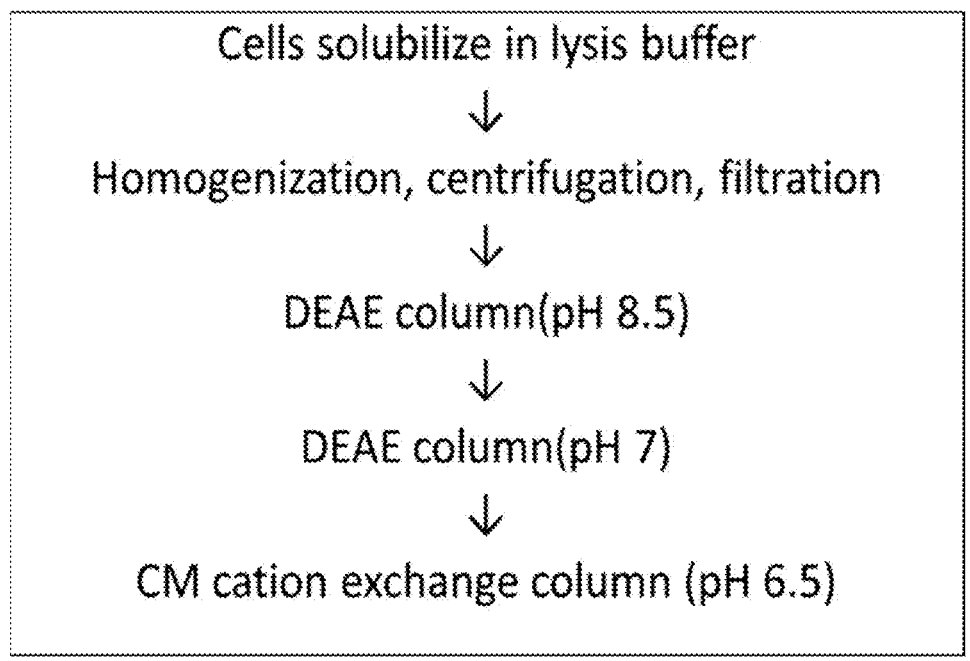
FIG. 3: A process flow chart summarizing a PpIX-TF conjugate (referred to herein as TF01) purification process according to one embodiment of the invention.

After the fermentation step is completed, the bacterial clones are harvested. In certain preferred embodiments, the harvesting comprises centrifuging the fermentation medium to form a cell pellet. To lyse the cells in the cell pellet, the cell pellet may be resuspended in a suitable lysis buffer and then homogenized. Preferably, the soluble fraction of the lysate is passed through a filter membrane before subsequent purification steps. Subsequent purification steps may include, for example, a series of chromatographic purifications to recover the porphyrin-protein conjugate. For example, when the desired porphyrin-protein conjugate is PpIX-TF, the PpIX-TF conjugate (TF01) may be recovered by passing the lysate through a first DEAE anion exchange column (pH 8.5), a second DEAE anion exchange column (pH 7.5), and a CM cation exchange column (pH 6.5) as shown in FIG. 3 and described in the Examples provided herein.

EXAMPLES

Example 1

Construction of 2α Globin and β Globin Expression Plasmid

SEQ ID NO: 1 and SEQ ID NO: 2 corresponding to human globin 2α and β chain sequences (i.e., the TF, 2αβ2 tetramer) were inserted into a pUC19 vector to generate a pUC19-2αβ plasmid along with the sequence for an expression protein (Ptac promoter). See FIG. 2. The plasmid was transformed into the Jm109(DE3), Clear coli and BL21 (DE3) E. coli strains and grown overnight at 37° C. Bacterial clones were identified using antibiotic selection (ampicillin, 100 μg/ml).

Example 2

Co-Expression of 2α Globin and β Globin by Fermentation

E. coli (Jm109(DE3), Clear coli and BL21(DE3)) clones transformed with pUC19-2αβ3 were inoculated into 200 ml of seed culture medium (yeast extract 6% and NaCl 1%) and cultivated at 37° C. with shaking at 250 rpm for overnight. The fermentation was performed in 10-L bioreactor (Sartorius C plus). The flask of seed culture was inoculated into 6.5 L of medium (yeast extract 1%, tryptone 1.6%, $K_2HPO_4$ 14.7 mM, $KH_2PO_4$ 37 mM, NaCl 15.1 mM, $(NH_4)_2SO_4$ 15.14 mM, L-proline 1.998 mM, glycerol 2%) in a 10-L bioreactor with a final $OD_{600}$ at 0.05 and cultivated at 32° C. and pH 7.0 with airflow of 6 L/min and initial stir rate at 400 rpm, in which dissolved oxygen was maintained above 30%.

The fed-batch process of recombinant protein production in 10-L bioreactor was divided into two phases. Phase I was aerobic batch cultivation at 32° C. for 7 h. Phase II was an induction process at 20° C. for 16 h using isopropyl-β-d-thiogalactoside (IPTG) at a final concentration of 0.4 μM with $OD_{600}$ of bacteria at 4.0 to induce the expression of recombinant protein. A fed-batch cultivation at 20° C. for 16 h in which 80 g/L glycerol was fed continuously to maintain the required specific growth rate of bacteria with airflow of 8 L/min and stir rate at 600-800 rpm, in which dissolved oxygen was maintained above 20%. The bacteria at final $OD_{600}$ of 30-40 were harvested by centrifugation and stored in −80° C. for future use.

Example 3

Purification of PpIX-TF Conjugates (TF01)

Cell Lysis and Clarification of Crude Sample

As illustrated by the process flow diagram in FIG. 3, the cell pellet from fermentation was resuspended in a solubilization buffer (20 mM Tris-HCl, pH 8.5) in 1 g cell to 10 ml buffer ratio. DNase was added to the suspension to a final concentration of 2 µg/ml and incubated at room temperature for 30 min. The suspension was then sonicated by Sonics Vibra-Cells™ sonicator at 70% amplitude for at least 10 min. For clarification, the cell lysate was centrifuged in a pre-chilled rotor at 35,000 g for at least an hour. The supernatant (soluble fraction) of the lysate was adjusted to pH 8.5 and conductivity to lower than 2.7 mS/cm. The supernatant was passed through a 0.45 pm PES filter membrane before loading onto chromatographic column.

Chromatographic Purification

To remove impurities from the conjugate, the soluble fraction which contained solubilized PpIX-TF conjugates (referred to herein as TF01) was passed through a series of chromatographic columns to isolate the PpIX-TF conjugates from various impurities.

First, the supernatant was loaded onto DEAE anion-exchange column which was pre-equilibrated with running buffer 1 (20 mM Tris-HCl, pH 8.5). After sufficient column wash with running buffer 1, the PpIX-TF conjugates (TF01) were eluted by several sodium chloride step elutions (5 mM NaCl, 1.5 CV; 10 mM NaCl, 3 CV; 20 mM NaCl, 1.5 CV; 40 mM NaCl, 2.5 CV; 100 mM NaCl, 1 CV; 1 M NaCl, 2 CV). The 40 mM NaCl elution fractions which contained the PpIX-TF conjugates (TF01) were collected.

Second, the recovered fraction was concentrated to 10 mg/ml and buffer-exchanged to running buffer 2 (25 mM potassium phosphate buffer, pH 7). The sample was then loaded onto a DEAE anion-exchange column which was pre-equilibrated with the running buffer 2. The PpIX-TF conjugates (TF01) appeared in the column flow-through during sample loading and column wash. After sufficient column wash with running buffer 2, the bound proteins were eluted by 1 M NaCl for 4 CV.

Third, the recovered fraction was adjusted to pH 6.5 and conductivity lower than 3.2 mS/cm. The PpIX-TF sample was then loaded onto CM cation exchange column which was pre-equilibrated with the running buffer 3. After sufficient column wash with running buffer 3, PpIX-TF conjugates (TF01) were eluted by several sodium chloride step elutions (0.25 M NaCl, 4 CV; 1 M NaCl, 4CV). The 0.25 M NaCl elution fractions which contained PpIX-TF (TF01) were collected.

Finally, the purified PpIX-TF (TF01) sample was concentrated to 30 mg/ml and then it was passed through a PALL Mustang™ E membrane for removal of endotoxin. The protein sample was sealed in a glass vial under deoxygenated environment. The glass vial was vacuum-sealed in a light-proof plastic bag and stored at 4° C.

Table 1 shows the results of five exemplary batches of PpIX-TF conjugates (TF01), made in accordance with the method provided in Examples 1-3. Isolated PpIX-TF conjugates (TF01) were suspended in 20 mM Tris buffer. PpIX and TF levels were measured using UPLC.

TABLE 1

Different Batches of PpIX-TF conjugates (TF01)

| PpIX-TF conjugate sample | PpIX level Conc. (mM) | Molar Ratio of PpIX to TF protein |
|---|---|---|
| Batch 1 | 0.054 | 0.690 |
| Batch 2 | 0.088 | 0.911 |
| Batch 3 | 0.062 | 0.619 |
| Batch 4 | 0.049 | 0.633 |
| Batch 5 | 0.177 | 0.705 |

Example 4

Characterization of PpIX-TF Conjugates (TF01)

Liquid Chromatography-Mass Spectrometry (LC-MS)

Figure 4:
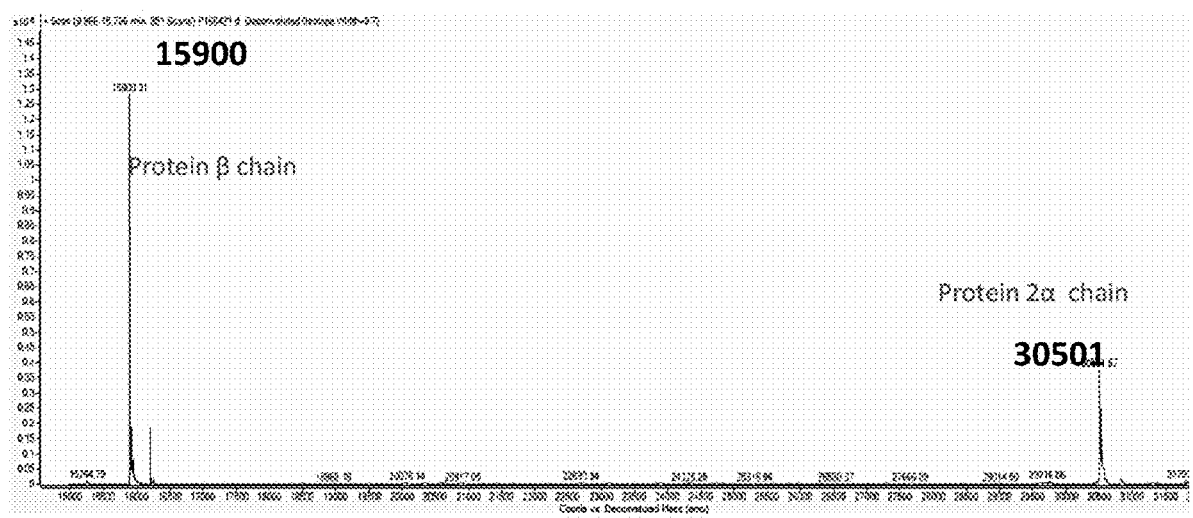
FIG. 4: The results of the analysis of purified TF (2αβ2 tetramer) and PpIX by LC-MS.
Figure 4:
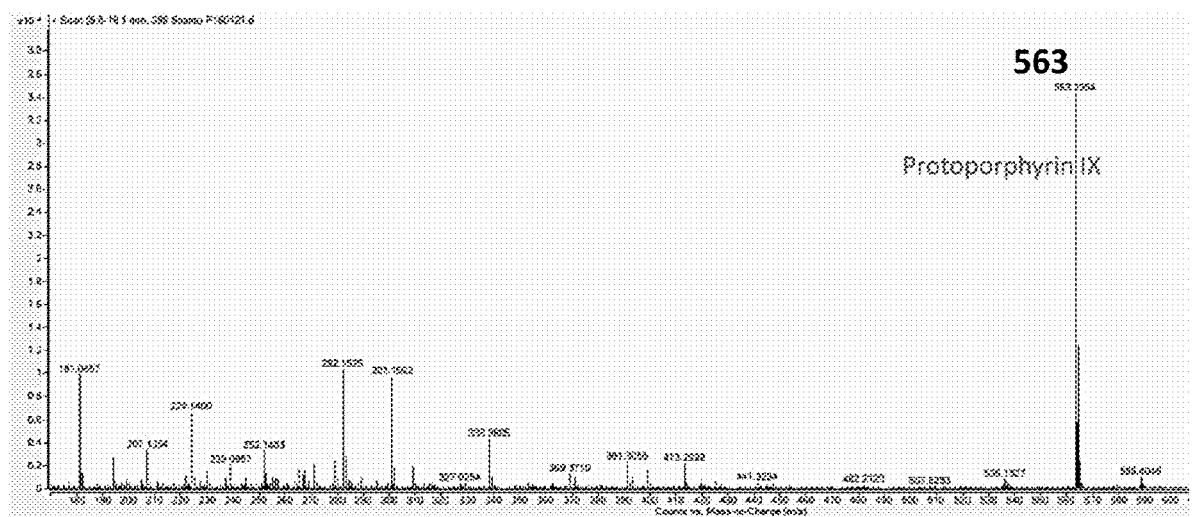

The purified protein was suspended in 100 µl and analyzed by LC-MS. FIG. 4 depicts the results of liquid chromatography-mass spectrometry which was used to measure the alpha chains, beta chains and PpIX content in the purified conjugate comprising PpIX and recombinant TF ($2\alpha\beta2$ tetramer) which was suspended in 100 µl after chromatographic purification step. FIG. 4(A) depicts the alpha chain and beta chain peaks, and FIG. 4(B) depicts the peaks associated with the PpIX portion of the purified recombinant protein, TF.

Ultra Performance Liquid Chromatography (UPLC)

The protein concentrations of the samples were measured by Bradford protein assay (Bradford Dye Reagent and Bovine Serum Albumin). Samples were diluted to protein concentration between 5-15 mg/ml. The purified protein was mixed with 400 µl acidic acetone (sample to organic solvent equals 1:8). After vigorous stirring, the mixture was separated by centrifugation. Acetonitrile (ACN, 400 µl, sample to organic solvent equals 1:8) was added into the solution, followed by centrifugation at 14,000 rpm for 5 min. Samples were then applied to ultra-performance liquid chromatography (UPLC) analysis (Acquity H-class UPLC system; Waters, Milford, Mass., USA).

PpIX was separated by Waters Acquity UPLC® BEH C18 1.7 µm, 2.1×50 mm Column at 0.50 ml/min at 25° C. for 15 min (Eluent: A: $H_2O$; B: ACN [0.1% TFA]) Gradient: 30% B to 50% B in 6 min, 50% B to 80% B in 12 min, 80% B to 30% B in 13 min, 30% B in 15 min. (Detection wavelength at 400 nm). Commercially obtained PpIX (Sigma-Aldrich, St. Louis, Mo., USA) was used as the standard. The peak of PpIX was identified and the peak area in the calibration standards and samples was recorded. The peak area of calibration standards was plotted against the PpIX concentration of working standards. Thus, the relative amount of PpIX was obtained using the calibration curve and associated equation.

Figure 5:
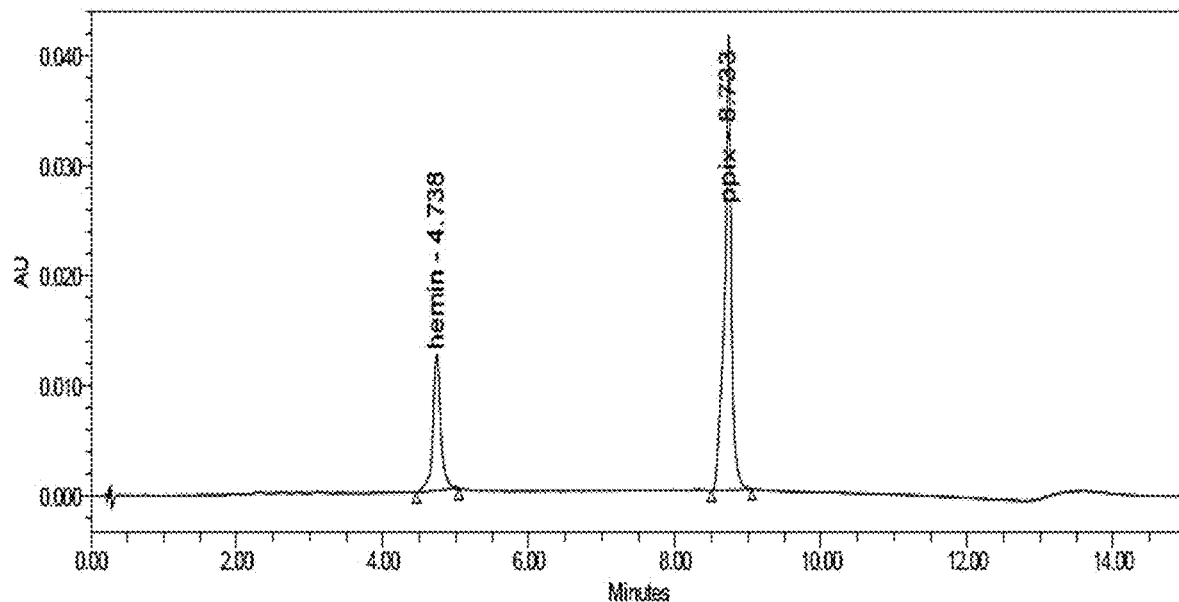
FIG. 5: The results of the ultra-performance liquid chromatography used to measure the amount of hemin and PpIX content in purified conjugate comprising PpIX and recombinant TF.

FIG. 5 depicts the results of the ultra-performance liquid chromatography used to measure the amount of hemin and PpIX content in purified conjugate comprising PpIX and recombinant TF (242 tetramer). FIG. 5 shows that the conjugate is comprised of over 70% PpIX compared to 26% hemin, indicating that there is a greater concentration of PpIX than hemin in the purified conjugate comprising PpIX and recombinant TF.

UV-Vis Absorption and Fluorescence Spectroscopy

A BMG fluostar spectrofluorophotometer was used to record fluorescent emissions of PpIX or PpIX-TF conjugate (referred to herein as TF01) suspended in aqueous buffer. A UV-vis spectrophotometer was used to record the absorbance spectra of PpIX and TF.

Figure 6:
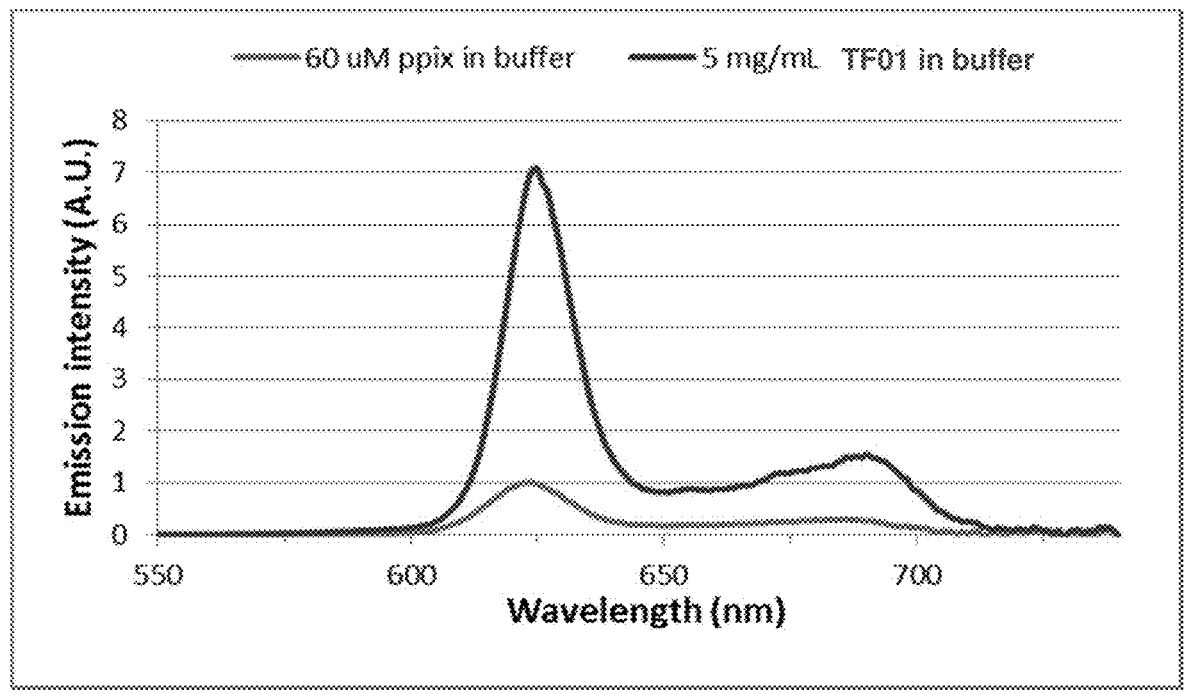
FIG. 6: Comparison of emission properties of the purified conjugate comprising PpIX-TF conjugate (TF01) solution and the control (PpIX in buffer).

FIG. 6 depicts the emission properties of the purified conjugate comprising PpIX and recombinant TF and the control (PpIX in buffer). FIG. 6 demonstrates that the emission properties of the recombinant protein TF bound to PpIX (top curve in FIG. 6, Batch 1, 5 mg/ml; corresponding to approximately 53 μM PpIX content) in Tris-HCl buffer (20 mM, pH 8.5; red) are greater than the emission properties of the control PpIX (bottom curve in FIG. 6, 60 μM PpIX) in Tris-HCl buffer (20 mM, pH 8.5, with 5% DMSO; blue).

Figure 7:
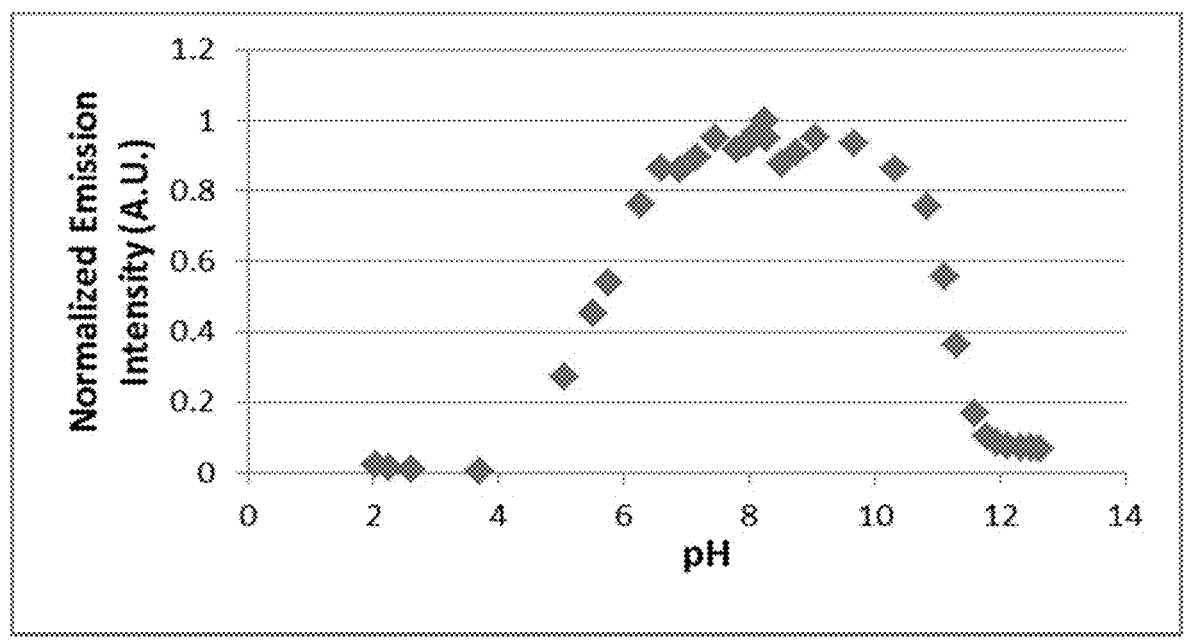
FIG. 7: An illustration of the emission properties of PpIX-TF conjugate (TF01) at different pH ranges.

FIG. 7 depicts the pH dependence of the emission intensity of TF in 50 mM Tris-HCl or potassium phosphate buffer when monitored at a $\lambda_{max}$=625 nm. Many studies suggest that the pH of solid tumors is around 7.0-7.2 whereas extracellular pH may be more acidic. FIG. 7 indicates that the PpIX-TF conjugate (TF01) of the invention is suitable for application in PDT therapy due to its wide pH range.

Solubility and Stability

Improvement in solubility and dispersibility of the PpIX-TF conjugate was compared to PpIX in aqueous Tris-HCl buffer, 20 mM, pH 8.5 (FIG. 6).

Cell Phototoxicity Assay

To determine cell viability under dark conditions, cells (1×10$^4$ cells/well) were seeded onto 96-well plates and incubated for 24 h at 37° C. After cell stabilization, the culture medium was replaced with 100 μl of culture medium containing free PpIX or PpIX-TF conjugate (referred to herein as TF01), followed by incubation for 24 h. The cells were then washed twice with serum-free medium and cell viability was evaluated by MTT assay after 48 h. To determine the in vitro phototoxicity after laser irradiation, cells (1×10$^4$ cells/well) were seeded onto 96-well plates and incubated for 24 h at 37° C. The cells were then treated with free PpIX or a PpIX-TF conjugate (TF01). After 24 h incubation, the cells were washed twice with serum-free medium and irradiated at a light intensity of 150 mW/cm$^2$ using 450 nm or 627 nm LED light source for 30 min or 10 mW/cm$^2$ using a 635-nm laser source for 5-30 min (3 J/cm$^2$ to 18 J/cm$^2$). The cell viability of irradiated cells was evaluated by MTT assay after 24 h of incubation.

Figure 8A:
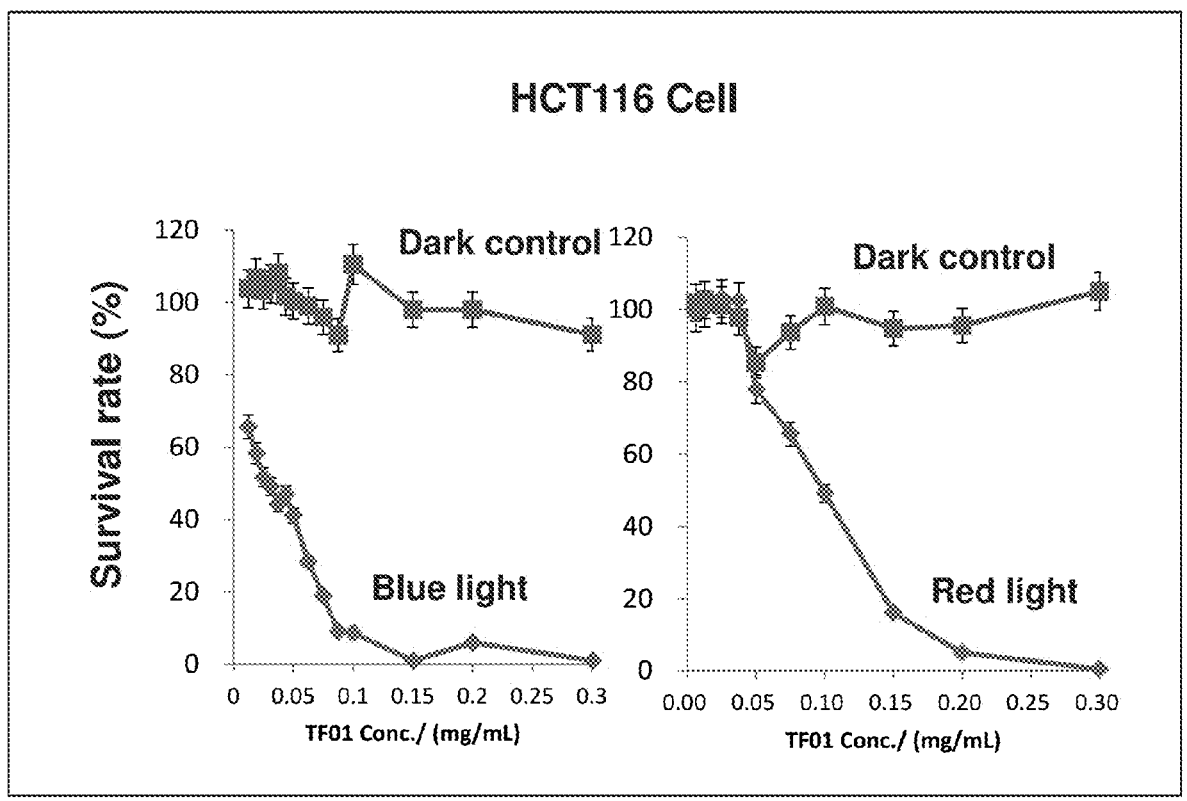
FIG. 8(a) shows the cytotoxicity of the PpIX-TF conjugate (TF01) under light excitation by blue light (450 nm laser source), by red light (627 nm laser source), and under dark conditions (control) in the HCT 116 (panel A) and HepG2 (panel B) cancer cell lines.
Figure 8A:
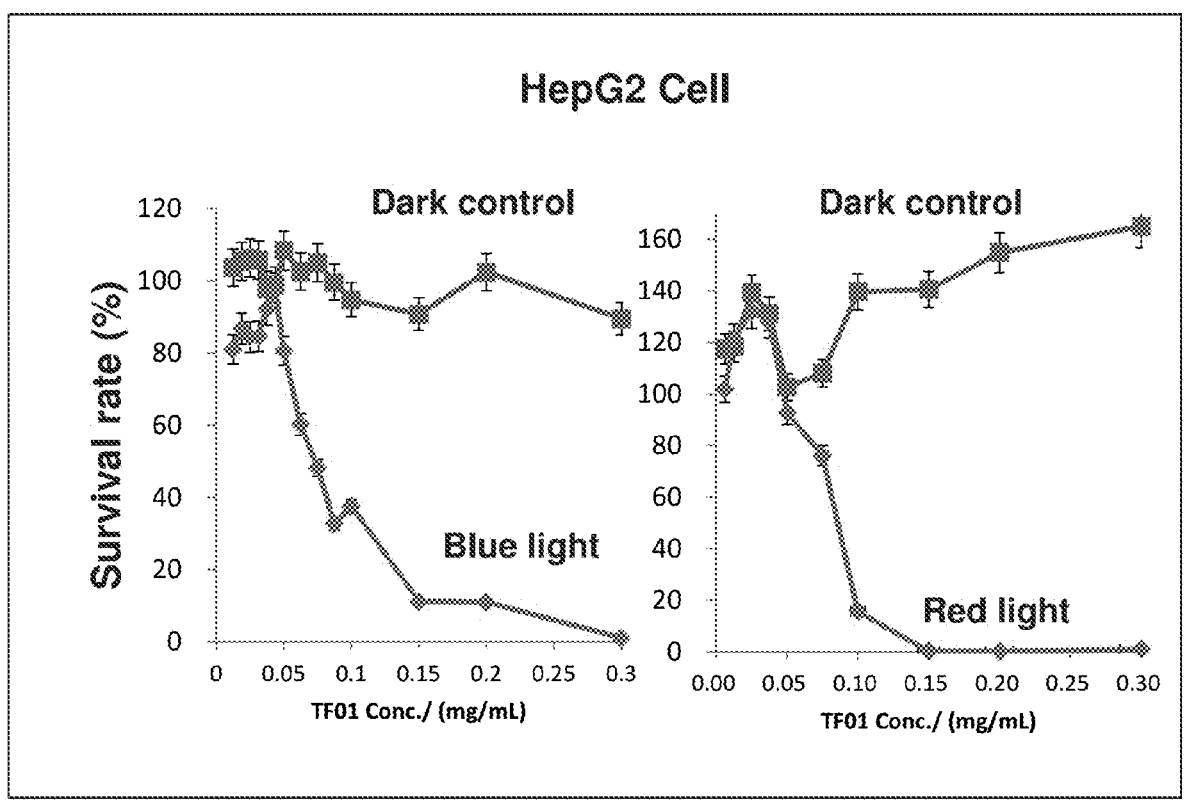
Figure 8B:
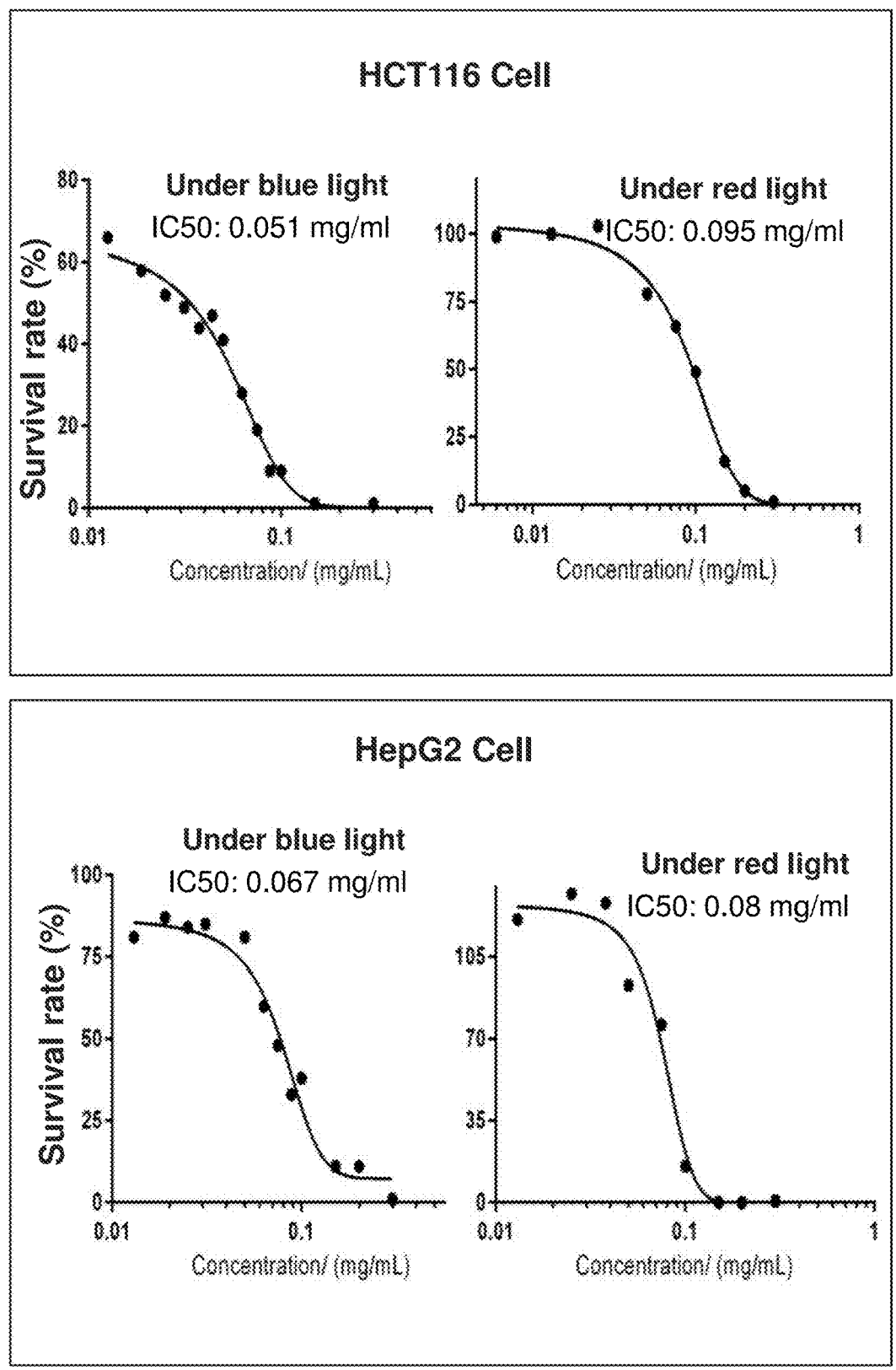
FIG. 8(b) shows $IC_{50}$ values determined by curve fitting-statistical software (GraphPad Prism 6) for the HCT116 (panel A) and HepG2 (panel B) cell lines under laser light excitation at 450 nm or 627 nm.

FIGS. 8(a) and 8(b) depict the cytotoxic effect of PpIX-TF conjugate (referred to herein as TF01) as demonstrated by the MTT assay. FIG. 8(a) shows the cytotoxicity of PpIX-TF conjugate (TF01) under light excitation (450 nm (blue) or 627 nm (red) light source) and under dark (control) is compared in two different cancer cell lines (A) HCT 116 and (B) HepG2. FIG. 8(b) shows the IC$_{50}$ values under light excitation (450 nm (blue) or 627 nm (red) light source), determined by curve fitting-statistical software (GraphPad Prism 6) in two different cancer cell lines (A) HCT 116 and (B) HepG2. For each cancer cell line, measurements were performed in dark and in the presence of 450 nm blue laser light or 627 nm red light. The data show that the survival rates of the cells from both cancer lines markedly decrease upon irradiation with the 450 nm blue laser light and 627 nm red laser light respectively when the PpIX-TF conjugate (TF01) concentration is greater than about 25 μg/ml.

Figure 16:
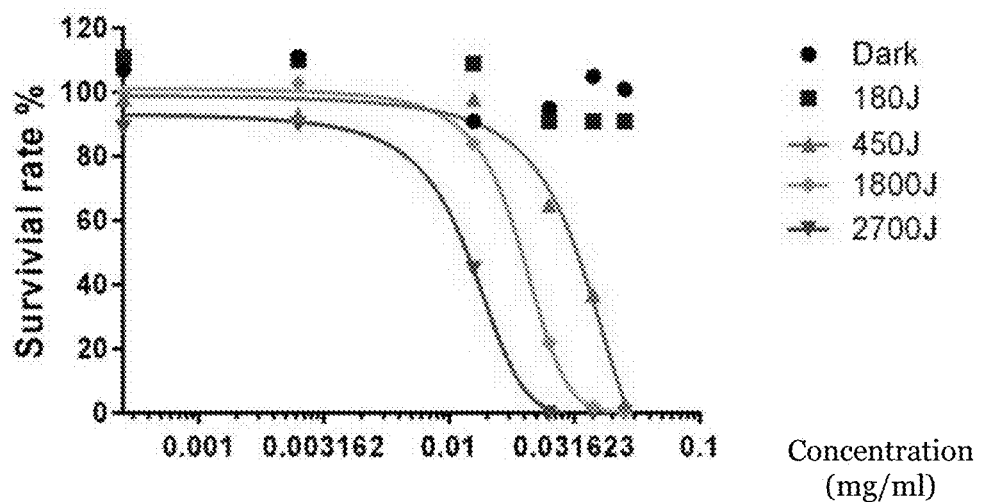
FIG. 16: $IC_{50}$ values of PpIX-TF conjugate (TF01) under different dosage of 635-nm laser excitation.

FIG. 16 shows the cytotoxicity of PpIX-TF conjugate (TF01) under different dosages of 635-nm laser excitation. The data show that the IC$_{50}$ values of PpIX-TF conjugate (TF01) were dosage dependent. When laser dosage were increased, the corresponding IC$_{50}$ values of PpIX-TF conjugate (TF01) were decreased.

Soft Agar Colony-Formation Assay

To estimate the anchorage-independent growth ability of cells treated by PpIX-TF conjugate (referred to herein as TF01), 3×10$^4$ cells of SK-Hep-1 cell were seeded in 35 mm dish and incubated for 24 h at 37° C. The cells were then treated with a PpIX-TF conjugate (TF01) or medium control. After 24 h incubation, the cells were washed twice with serum-free medium and irradiated at a light intensity of 10 mW/cm$^2$ using a 635-nm laser source for 5 min. Then, 5000 cells were suspended in 0.3% noble agar and cells were allowed to grow for another 2 weeks. Colonies were stained with 0.02% Giemsa Stain Solution, and documented by scanning.

Figure 11:
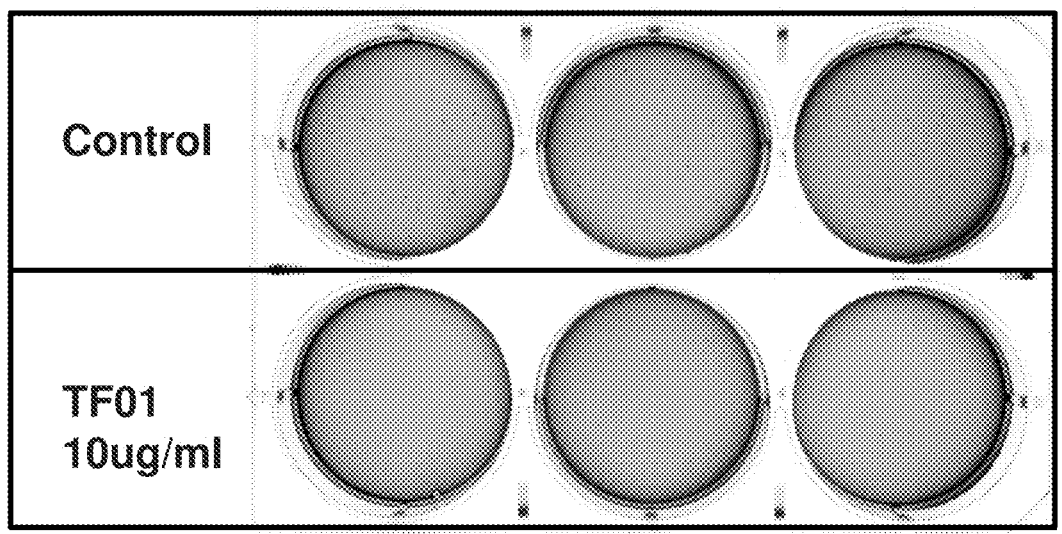
FIG. 11: The results of a soft agar colony-formation assay showing the effect of PpIX-TF conjugates (TF01) at a concentration of 10 ug/ml on the formation of SK-Hep-1 cancer cell colony by comparison with a medium control.

FIG. 11 depicts the anti-colony-formation effect of PpIX-TF conjugate (TF01) as demonstrated by the soft agar colony-formation assay. Treated cells by 10 ug/ml of PpIX-TF conjugate (TF01) and irradiated at a light intensity 3 J/cm$^2$ using a 635-nm laser source will significantly inhibit the cancer cell soft agar colony formation.

Cell Uptake and Imaging

Cancer cells were used to detect and compare cellular uptake of PpIX and PpIX-TF conjugate (referred to herein as TF01) in vitro. The cells were cultured in medium supplemented with 10% fetal bovine serum at 37° C. and 5% CO$_2$. After incubating cells with PpIX-TF conjugate (TF01), images were viewed by confocal microscopy.

Figure 9:
FIG. 9: Fluorescence microscopic image showing cellular uptake of PpIX-TF conjugates (TF01) in a colorectal carcinoma cell line HCT116.

FIG. 9 depicts the fluorescence microscopic analysis of cellular uptake of recombinant TF in a colorectal carcinoma cell line HCT116. The intense fluorescent signals of the purified PpIX-TF conjugates (TF01) in FIG. 9 reveals that the PpIX-TF conjugates (TF01) are widely distributed in the cytoplasm of the colorectal carcinoma cells (represented by arrows in the micrograph).

Figure 12:
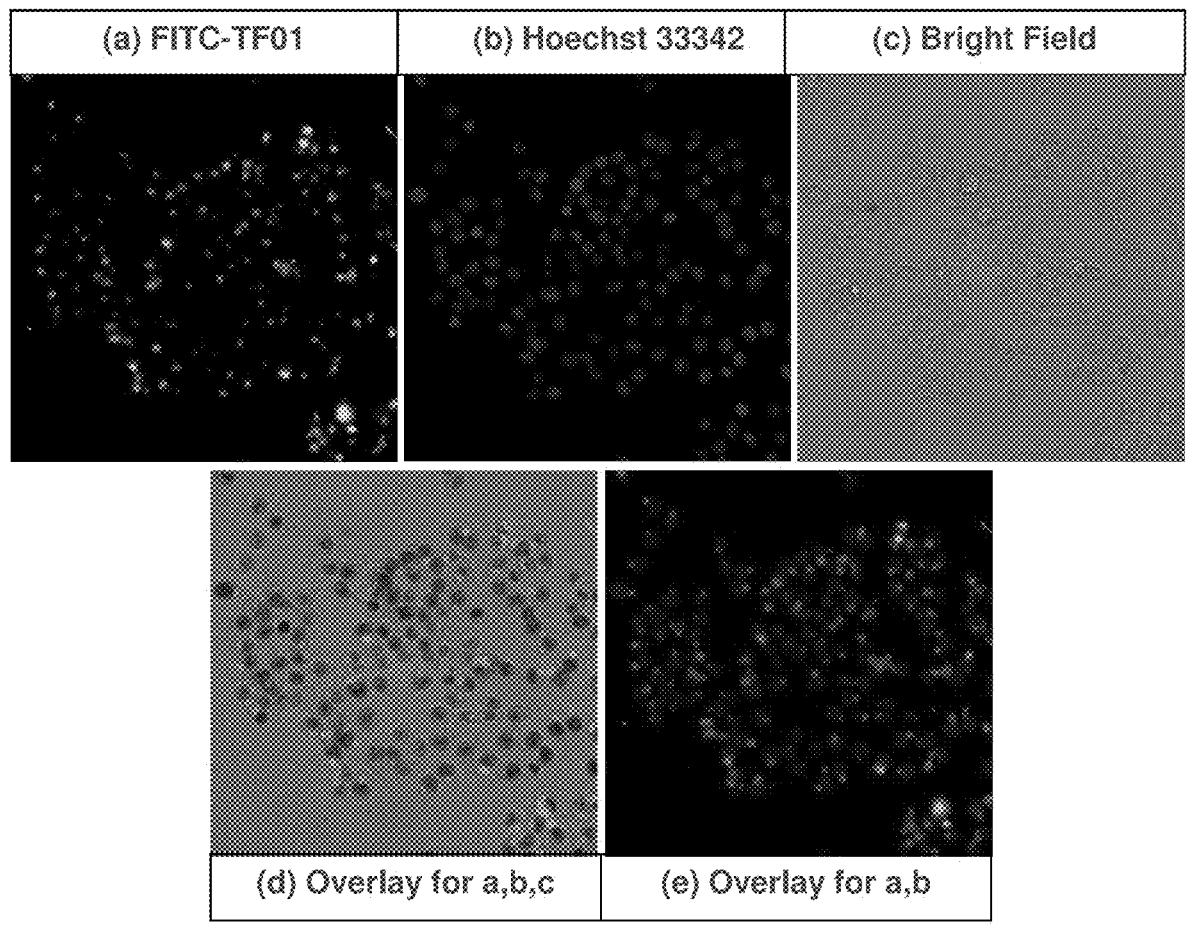
FIG. 12: shows cellular uptake of PpIX-TF conjugate (TF01) in a liver cancer cell line HepG2 using (a) FITC labeling; (b) Hoechst 33342 staining; (c) Bright Field, microscopy techniques; (d) overlay for (a), (b) and (c); and (e) overlay for (a) and (b).

FIG. 12 shows the cellular uptake of PpIX-TF conjugate (TF01) in a liver cancer cell line HepG2. PpIX-TF conjugates (TF01) were labeled with FITC, stained with Hoechst 33342 or illuminated using Bright field microscopy; the results of such labeling, staining and microscopy techniques are depicted in figures (a)-(e):(a) FITC-TF01; (b) Hoechst 33342; (c) Phase contrast, Bright field; (d) overlay the images of (a), (b) & (c); and (e) overlay the images of (a) & (b).

Figure 13:
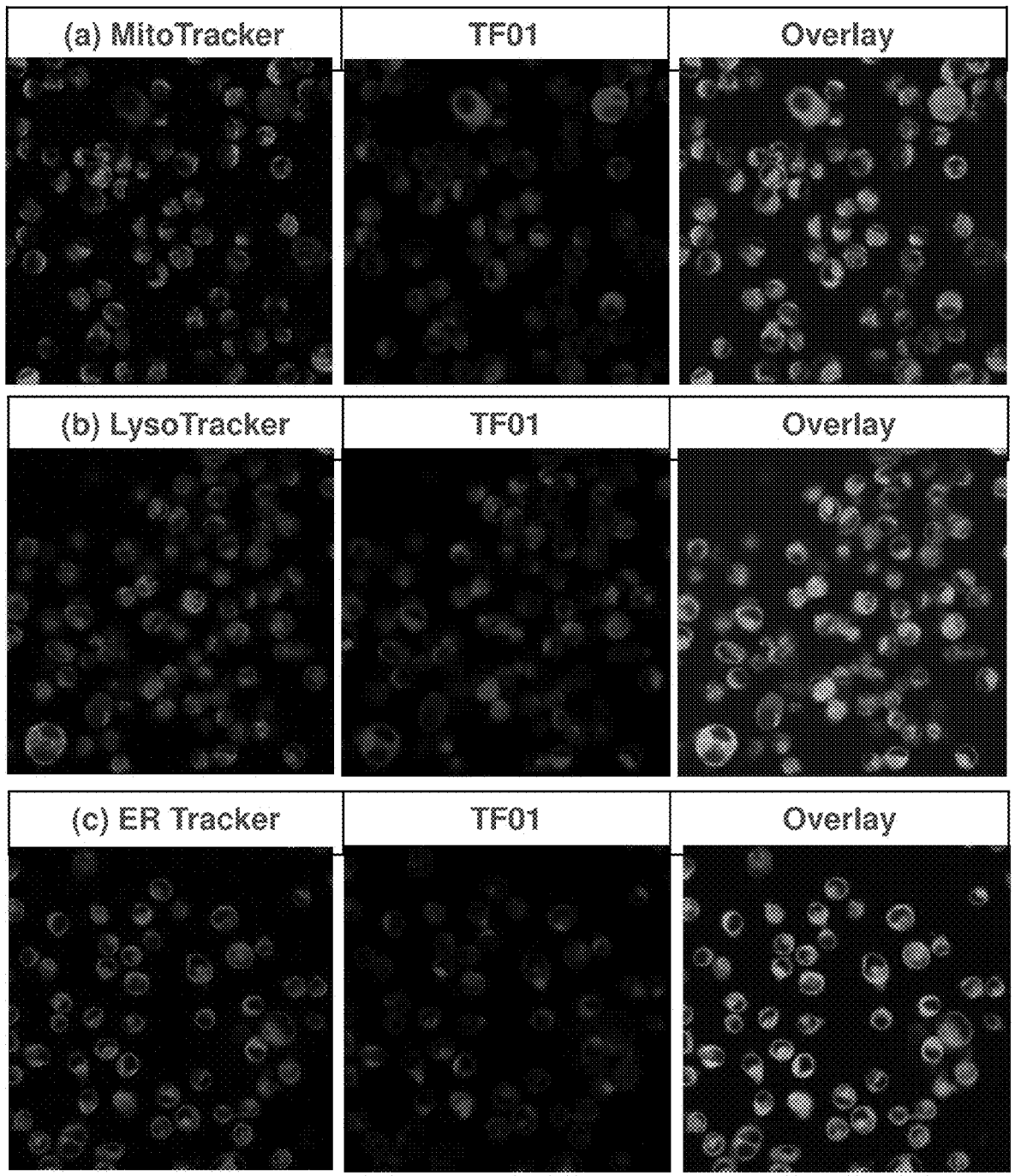
FIG. 13: shows cellular localization of PpIX-TF conjugate (TF01) in a liver cancer cell line SK-Hep-1 using MitoTracker (a); LysoTracker (b); and ER Tracker (c) labeling techniques.

FIG. 13 shows cellular localization of PpIX-TF conjugate (TF01) in a liver cancer cell line SK-Hep-1. The Mitotracker, lysotracker and ER-tracker (Thermo Fisher Scientific) were used to label mitochondria, lysosome and endoplasmic reticulum (ER) respectively. Two measures of correlation, the Pearson correlation coefficient (PCC) and the Mander's overlap coefficient (MOC) were calculated as depicted in the table below. The results demonstrated the co-localization of PpIX-TF conjugates (TF01) in different organelles of the cell: mitochondria, lysosome and endoplasmic reticulum.

|  | Pearson correlation coefficient (PCC) | Mander's overlap coefficient (MOC) |
| --- | --- | --- |
| Mitochondria | 0.4922 | 0.4684 |
| Lysosome | 0.4974 | 0.4866 |
| Endoplasmic reticulum | 0.6076 | 0.6908 |

Reactive Oxygen Species (ROS) Generation

To determine singlet oxygen generation, singlet oxygen detection method was applied to a 3 ml aqueous solution containing the singlet oxygen generator, 50 M of RNO and 8 mM of imidazole. The detection for absorption intensity of RNO near 440 nm was monitored to reflect the production of ROS by a UV-vis spectrophotometer after time intervals of laser exposure.

Figure 10:
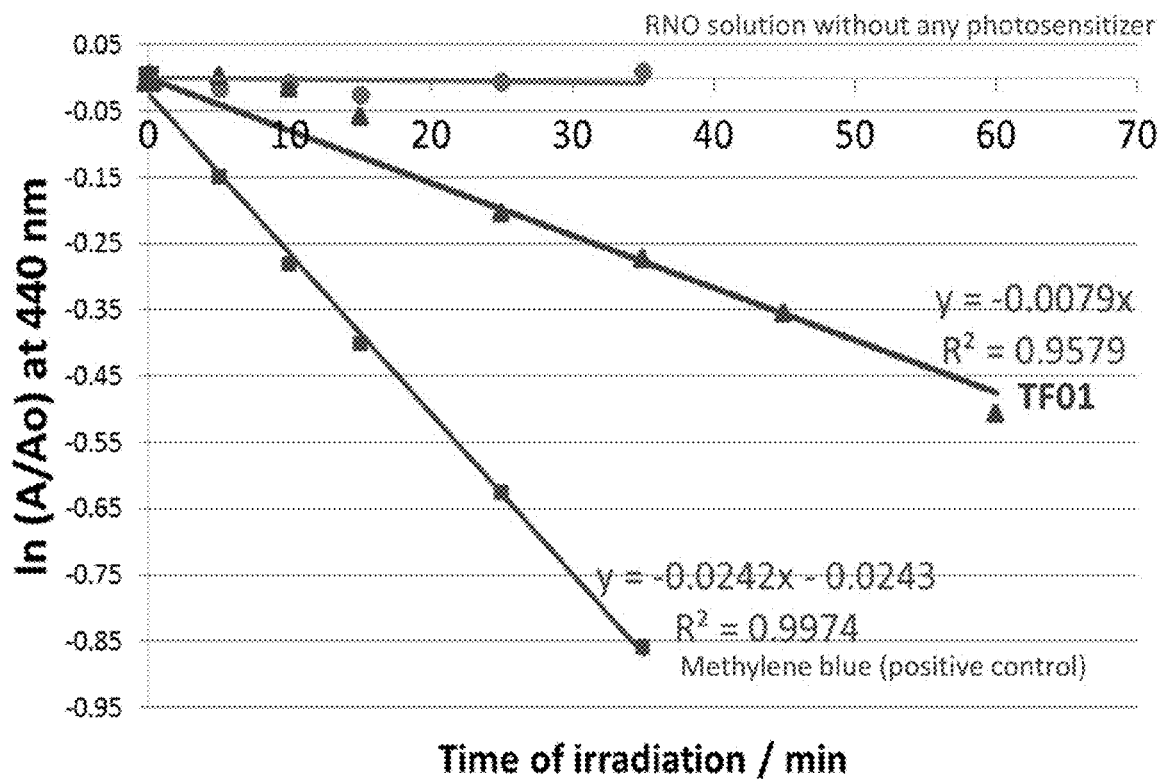
FIG. 10: Measurement of generation of reactive oxygen species by PpIX-TF conjugates (TF01) by comparison with photocatalytic bleaching of p-nitrosodimethylaniline (RNO).

FIG. 10 depicts the ROS generation by the conjugate comprising PpIX and PpIX-TF conjugate (referred to herein as TF01) against the positive control of methylene blue. FIG. 10 depicts that the quantum yield of ROS of the conjugate of PpIX and recombinant TF was almost double that of methylene blue. These results indicate that the conjugate would be effective as a photosensitizer in PDT or PDD.

To examine intracellular ROS generation by PpIX and PpIX-TF conjugate (TF01), HCT116 cells were seeded in 24-well, glass-bottomed plate and incubated with cellrox reagent (Thermo Fisher Scientific). After 30 min, the cells were washed three times by PBS and treated with PpIX or PpIX-TF conjugate (TF01). After 24 h of incubation, the cells were washed twice with PBS and then exposed to a 10 mW/cm$^2$ using a 635-nm laser source for 30 min. After irradiation, the fluorescence intensity of cells was measured by a microplate reader with excitation/emission at 485/520 nm. The values are expressed as fluorescence intensity ratio to control.

Figure 14:
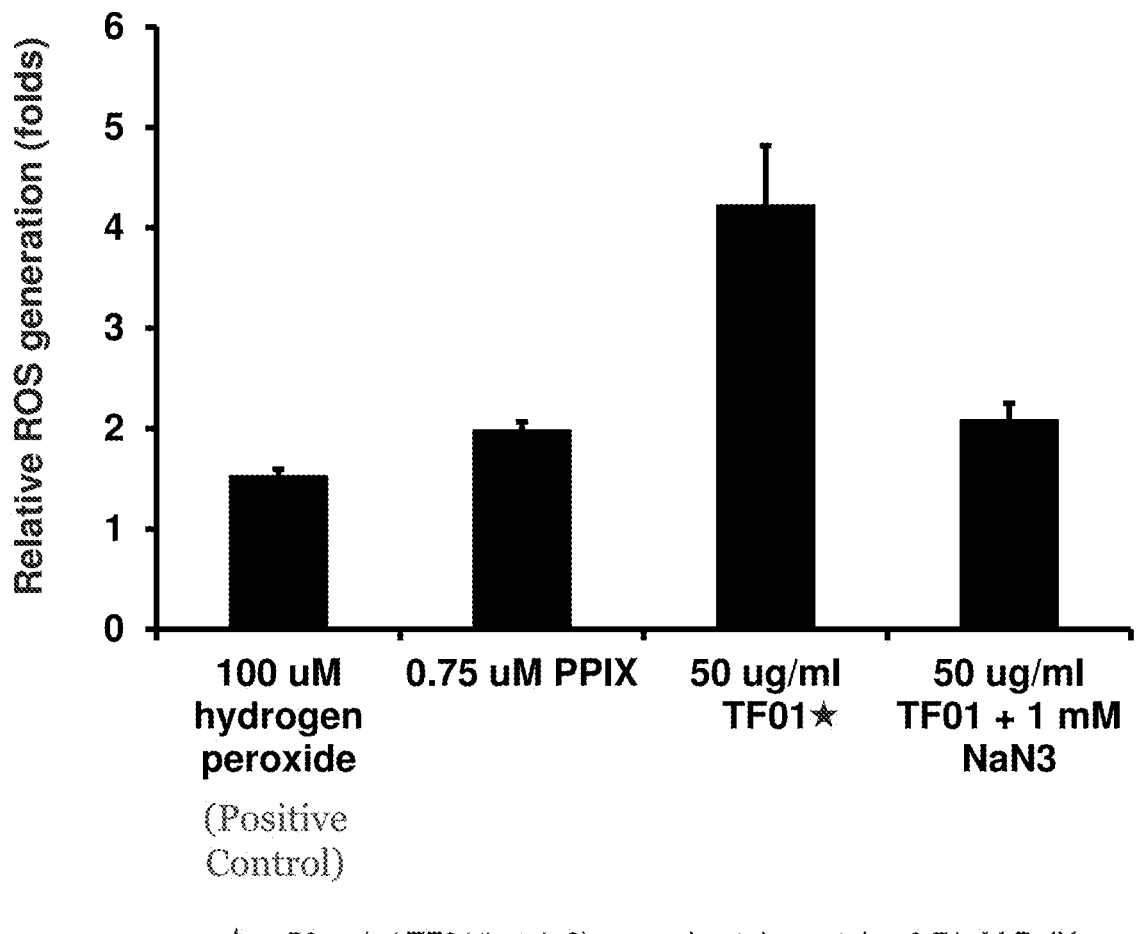
FIG. 14: Measurement of intracellular reactive oxygen species generation by the PpIX-TF conjugate (TF01) in HCT116 cancer cells.

FIG. 14 depicts the intracellular ROS generation by the PpIX-TF conjugate (TF01) in the HCT116 cancer cells. 100 uM $H_2O_2$, as a positive control, increase the intracellular ROS generation. PpIX-TF conjugates (TF01) (50 um/ml (batch 2) contains approximately 0.71 uM PpIX) greatly enhance the intracellular ROS generation, which is much higher than the intracellular ROS generation of the control PpIX (at a concentration of 0.75 uM). Sodium azide ($NaN_3$, a scavengers of ROS), the specific quencher of $^1O_2$, can partially abolish this effect.

Example 5

In Vivo PDT Efficacy

Figure 15:
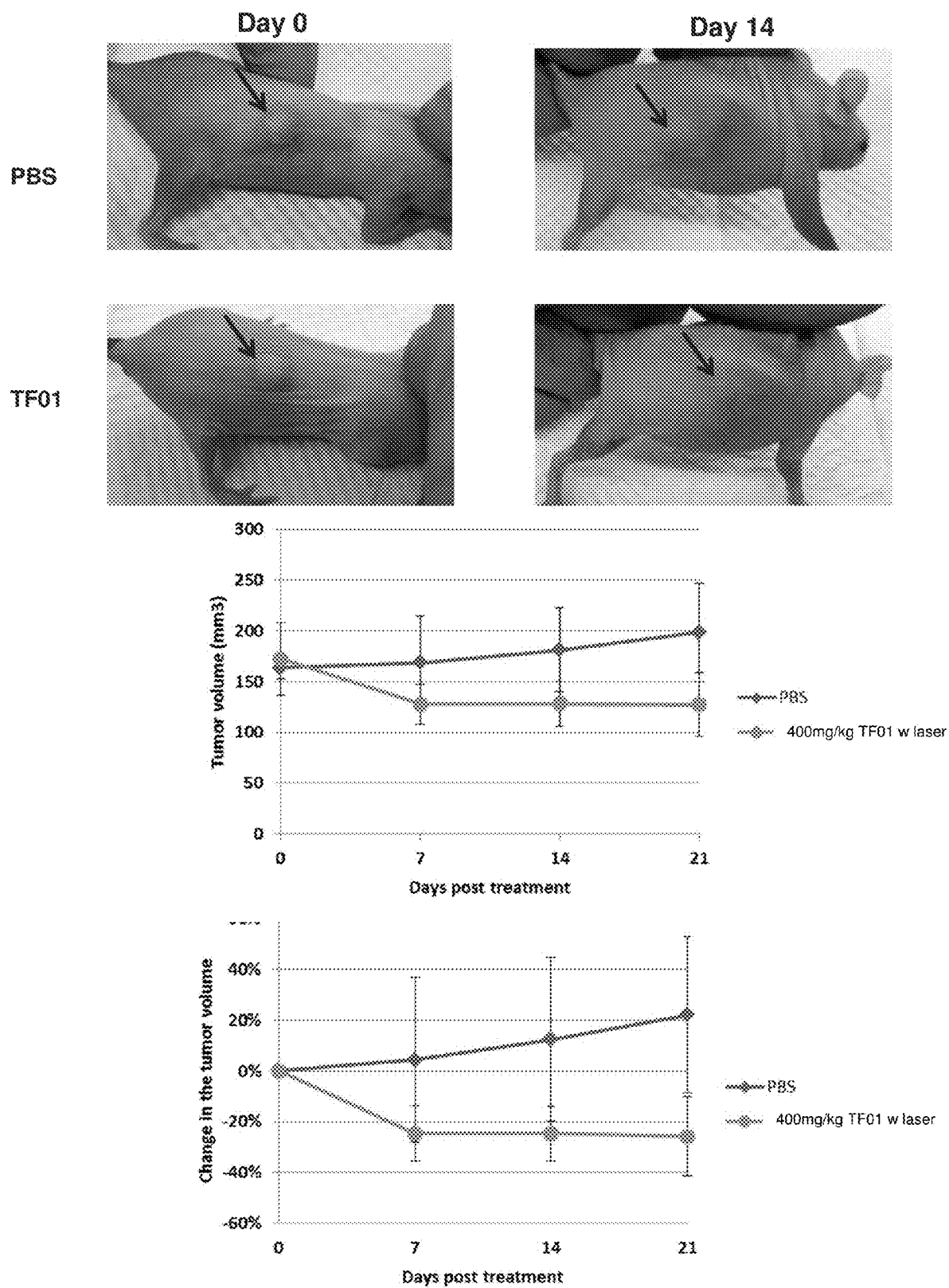
FIG. 15: shows in vivo PDT efficacy of PpIX-TF conjugate (TF01) in nude mice by reduction in tumor volume.

To test the in vivo PDT efficacy of PpIX-TF conjugate, nude mice bearing human hepatoma SK-HEP 1 xenograft were intravenously treated with PBS, 200 mg/kg or 400 mg/kg PpIX-TF conjugate (TF01) respectively (n=3-4 per group), followed by the laser application (at a light intensity 230 mW/cm$^2$, 260 J/cm$^2$, using a 635-nm laser source). Visible tumors were measured using two orthogonal measurements L and W (perpendicular to L), the volumes were calculated using the formula V=LW2/2 and recorded. FIG. 15 shows the representative digital photos of tumors before and after treatment. The figure shows the absolute tumor volumes (upper panel) and their percentage changes (lower panel). The treatment with 400 mg/kg TF01 followed by the laser application results in tumor regression.

While the above described embodiments of the invention are described in terms of preferred ranges, these preferences are by no means meant to limit the invention. As would be readily understood by one skilled in the art, the preferred amounts and ingredients used in the pharmaceutical compositions depend on the method of administration, the conjugate used, and the like. Likewise, actual release rates and release duration depend on a variety of factors in addition to the above, such as the disease state being treated, the age and condition of the patient, the route of administration, as well as other factors which would be readily apparent to those skilled in the art. All of the foregoing U.S. Patents and other publications are expressly incorporated by reference herein in each of their entireties.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

SEQ ID NO: 1: Protein Sequence of 2α Chain of TF
MLSPADKTNVKAAWGKVGAHAGEYGAEALER-
MFLSFPTTKTYFPHFDLSHGSAQVKG HGKKVADAL-
TNAVAHVDDMPNALSALSDLHAHKLRVDPV-
NFKLLSHCLLVTLAAHLP AEFTPAVHASLDK-
FLASVSTVLTSKYRGMLSPADKTNVKAAWGKVGA-
HAGEYGAEAL ERMFLSFPTTKTYFPHFDLSHGS-
AQVKGHGKKVADALTNAVAHVDDMPNALSALSDLH
AHKLRVDPVNFKLLSHCLLVTLAAHLPAEFTPAVHA-
SLDKFLASVSTVLTSKYR SEQ ID NO: 2: Protein Sequence of β Chain of TF
MHLTPEEKSAVTALWGKVNVDEVGGEALGRLL-
VVYPWTQRFFESFGDLSTPDAVMGN PKVKAHG-
KKVLGAFSDGLAHLDNLKGTFATLSELHCDK-
LHVDPENFRLLGNVLVCVLA HHFGKEFTPPVQAA-
YQKVVAGVANALAHKYH SEQ ID NO: 3: Myoglobin
MGLSDGEWQLVLNVWGKVEADIPGHGQEV-
LIRLFKGHPETLEKFDKFKHLKSEDEMKA SEDLKKH-
GATVLTALGGILKKKGHHEAEIKPLAQSHATKHKIPV-
KYLEFISECIIQVLQSK HPGDFGADAQGAMNKALE-
LFRKDMASNYKELGFQG SEQ ID NO: 4: Cytochrome P450
MINMGDSHVDTSSTVSEAVAEEVSLFSMTDMILF-
SLIVGLLTYWFLFRKKKEEVPEFTKI QTLTSSVRES-
SFVEKMKKTGRNIIVFYGSQTGTAEEFANRLSKDAH-
RYGMRGMSADPEE YDLADLSSLPEIDNALVVFC-
MATYGEGDPTDNAQDFYDWLQETDVDLSGVK-
FAVFGLG NKTYEHFNAMGKYVDKRLEQLG-
AQRIFELGLGDDDGNLEEDFITWREQFWPAVCEHFG
VEATGEESSIRQYELVVHTDIDAAKVYMGEMGR-
LKSYENQKPPFDAKNPFLAAVTTNR KLNQGTER-
HLMHLELDISDSKIRYESGDHVAVYPAND-
SALVNQLGKILGADLDVVMSL NNLDEESNK-
KHPFPCPTSYRTALTYYLDITNPPRTNVLYELAQYA-
SEPSEQELLRKMASS SGEGKELYLSWVVEAR-
RHILAILQDCPSLRPPIDHLCELLPRLQARYYSIASSS-
KVHPNSV HICAVVVEYETKAGRINKGVATNWL-
RAKEPAGENGGRALVPMFVRKSQFRLPFKATTP
VIMVGPGTGVAPFIGFIQERAWLRQQGKEVGETLLY-
YGCRRSDEDYLYREELAQFHRDG ALTQLNVAFS-
REQSHKVYVQHLLKQDREHLWKLIEGGAHIYVCG-
DARNMARDVQNTF YDIVAELGAMEHAQAVDYI-
KKLMTKGRYSLDVWS SEQ ID NO: 5: Cytochrome C
MGDVEKGKKIFIMKCSQCHTVEKGGKHKTGPNL-
HGLFGRKTGQAPGYSYTAANKNKGI IWGEDTLMEY-
LENPKKYIPGTKMIFVGIKKKEERADLIAYLKKATNE SEQ ID NO: 6: Nitric Oxide Synthase (Isoform 1)
MEDHMFGVQQIQPNVISVRLFKRKVGGLGFLVK-
ERVSKPPVIISDLIRGGAAEQSGLIQA GDIILAVNGR-
PLVDLSYDSALEVLRGIASETHVVLILRGPEGFTTH-
LETTFTGDGTPKTIR VTQPLGPPTKAVDLSH-
QPPAGKEQPLAVDGASGPGNGPQHAYDDGQEAGSL-
PHANGLA PRPPGQDPAKKATRVSLQGRGEN-
NELLKEIEPVLSLLTSGSRGVKGGAPAKAEMKDMGI
QVDRDLDGKSHKPLPLGVENDRVFNDLWG-
KGNVPVVLNNPYSEKEQPPTSGKQSPTKN GSPSK-
CPRFLKVKNWETEVVLTDTLHLKSTLETGCTEY-
ICMGSIMHPSQHARRPEDVRT KGQLFPLAKEFIDQY-
YSSIKRFGSKAHMERLEEVNKEIDTTSTYQLKDT-
ELIYGAKHAWR NASRCVGRIQWSKLQVFDARDCT- TAHGMFNYICNHVKYATNKGNLRSAITIFPQRTDG KHDFRVWNSQLIRYAGYKQPDGSTLGDPANVQFTEI- CIQQGWKPPRGRFDVLPLLLQAN GNDPELFQIPPEL- VLEVPIRHPKFEWFKDLGLKWYGLPAVSNMLLEIG- GLEFSACPFSGW YMGTEIGVRDYCDNSRY- NILEEVAKKMNLDMRKTSSLWKDQALVEINI- AVLYSFQSDK VTIVDHHSATESFIKHMENEYR- CRGGCPADWVWIVPPMSGSITPVFHQEMLN- YRLTPSF EYQPDPWNTHVWKGTNGTPTKR- RAIGFKKLAEAVKFSAKLMGQAMAKRVKATILYAT ETGKSQAYAKTLCEIFKHAFDAKVMSMEEYDIVHLE- HETLVLVVTSTFGNGDPPENGEK FGCALMEM- RHPNSVQEERKSYKVRFNSVSSYSDSQKSSGDG- PDLRDNFESAGPLANVR FSVFGLGSRAYPHFCAF- GHAVDTLLEELGGERILKMREGDELCGQEEAFRT- WAKKVFK AACDVFCVGDDVNIEKANNSLISNDR- SWKRNKFRLTFVAEAPELTQGLSNVHKKRVSA ARLLSRQNLQSPKSSRSTIFVRLHTNGSQELQY- QPGDHLGVFPGNHEDLVNALIERLEDA PPVNQMVKVELLEERNTALGVISNWTDELRLPPCTI- FQAFKYYLDITTPPTPLQLQQFAS LATSEKEKQRLL- VLSKGLQEYEEWKWGKNPTIVEVLEEFPSIQM- PATLLLTQLSLLQPRY YSISSSPDMYPDEVHLT- VAIVSYRTRDGEGPIHHGVCSSWLNRIQADELVPC- FVRGAPSF HLPRNPQVPCILVGPGTGIAPFRSFWQ- QRQFDIQHKGMNPCPMVLVFGCRQSKIDHIYRE ETLQAKNKGVFRELYTAYSREPDKPKKYVQDILQEQ- LAES VYRALKEQGGHIYVCGDV TMAADVLKAI- QRIMTQQGKLSAEDAGVFIS RMRDDNRYHED- IFGVTLRTYEVTNRLRSE SIAFIEESKKDTDEVFSS SEQ ID NO: 7: Nitric Oxide Synthase (Isoform 2)
MACPWKFLFKTKFHQYAMNGEKDINNNVEKAP- CATSSPVTQDDLQYHNLSKQQNESP QPLVETGKKSP- ESLVKLDATPLSSPRHVRIKNWGSGMTFQDTLHHI- CAKGILTCRSKSCL GSIMTPKSLTRGPRDKPT- PPDELLPQAIEFVNQYYGSFKEAKIEEHLARVEAVTI- CEIETTG TYQLTGDELIFATKQAWRNAPRCI- GRIQWSNLQVFDARSCSTAREMFEHICRHVRYSTN NGNIRSAITVFPQRSDGKHDFRVWNAQLIRY- AGYQMPDGSIRGDPANVEFTQLCIDLGW KPKYGRFDVVPLVLQANGRDPELFEIPPDLVL- EVAMEHPKYEWFRELELKWYALPAVA NMLLEVG- GLEFPGCPFNGWYMGTEIGVRDFCDVQRYNI- LEEVGRRMGLETHICLASLW KDQAVVEINI- AVLHSFQKQNVTIMDHHSAAESFMKYMQNEYR- SRGGCPADWIWLVPP MSGSITPVFHQEMLNYVL- SPFYYYQVEAWKTHVWQDEKRRPICRREIPLKVLVI- CAVLFA CMLMRKTMASRVRVTILFATETGKSE- ALAWDLGALFSCAFNPKVVCMDKYRLSCLEEE RLLLVVTSTFGNGDCPGNGEKLKKSLFMLKELNN- KFRYAVFGLGSSMYPRFCAFAHDID QICLSHL- GASQLTPMEGDELSGQEDAFRSWAVQTFICAACE- TFDVRGKQHIQIPICLYTSN VTWDPHHY- RLVQDSQPLDLSKALSSMHAKNVFTMRLKSRQNL- QSPTSSRATILVELSCE DGQGL- NYLPGEHLGVCPGNQPALVQGILERVVDGP- TPHQTVRLEALDESGSYWVSDKR LPPCSLSQAL- TYFLDITTPPTQLLLQKLAQVATEEPERQRLEALCQP- SEYSKWICFTNSPTF LEVLEEFPSLRVSAGFLL- SQLPILKPRFYSISSSRDHTPTEIHLTVAVVT- YHTRDGQGPLHH GVCSTWLNSLKPQDPVPCFVR- NASGFHLPEDPSHPCILIGPGTGIAPCRRPEDHIYQEEM- RLHDSQ HKGVRGGRMTLVFGCRRPDEDHIYQEEM- LEMAQKGVLHAVHTAYSRLPGKPKVYVQ DILRQQLASEVLRVLHKEPGHLYVCGDVRMARD- VAHTLKQLVAAKLKLNEEQVEDYF FQLKSQKRYH- EDIFGAVFPYEAKKDRVAVQPSSLEMSAL SEQ ID NO: 8: Nitric Oxide Synthase (Isoform 3)
MGNLKSVAQEPGPPCGLGLGLGLGLCGKQGPATPA- PEPSRAPASLLPPAPEHSPPSSPLT QPPEGPKF- PRVKNWEVGSITYDTLSAQAQQDGPCTPRR- CLGSLVFPRKLQGRPSPGPPAP EQLLSQARD- FINQYYSSIKRSGSQAHEQRLQEVEAEVAATGTYQL- RESELVFGAKQAWR NAPRCVGRIQWGKLQVF- DARDCRSAQEMFTYICNHIKYATNRGNLR- SAITVFPQRCPGR GDFRIWNSQLVRYAGYRQ- QDGSVRGDPANVEITELCIQHGWTPGNGRFDV- LPLLLQAP DDPPELFLLPPELVLEVPLEHPTLEW- FAALGLRWYALPAVSNMLLEIGGGLEFPAAPFSGW YMSTEIGTRNLCDPHRYNILEDVAVCMDLDT- RTTSSLWKDKAAVEINVAVLHSYQLAK VTIVDHH- AATASFMKHLENEQKARGGCPADWAWIVPPIS- GSLTPVFHQEMVNYFLSPAF RYQPDPWKG- SAAKGTGITRKKTFKEVANAVKISASLMGTV- MAKRVKATILYGSETGRA YAQQLGRLFRKAF- DPRVLCMDEYDVVSLEHETLVLVVTSTFGNGDP- PENGESFAAA LMEMSGPYNSSPRPEQHKSYKIRFN- SISCSDPLVSSWRRKRKESSNTDSAGALGTLRFCV FGLGSRAYPHFCAFARAVDTRLEELGGER- LLQLGQGDELCGQEEAFRGWAQAAFQAAC ETFCVGEDAKAAARDIFSPKRSWKRQRYRYLSAQAE- GLQLLPGLIHVHRRKMFQATIRSV ENLQSSKSTRA- TILVRLDTGGQEGLQYQPGDHIGVCPPNRPG- LVEALLSRVEDPPAPTEP VAVEQLEKGSPGGPP- PGWVRDPRLPPCTLRQALTFFLDITSPPSPQLLRLLST- LAEEPREQ QELEALSQDPRRYEEWKWFRCPT- LLEVLEQFPSVALPAPLLLTQLPLLQPRYYSVSSAPS THPGEIHLTVAVLAYRTQDGLGPLHYGVCSTWLSQ- LKPGDPVPCFIRGAPSFRLPPDPSL PCILVGPGTGIAP- FRGFWQERLHDIESKGLQPTPMTLVFGCRCSQLDH- LYRDEVQNAQQ RGVFGRVLTAFSREPDNPKT- YVQDILRTELAAEVHRVLCLERGHMFVCGDVT- MATNVL QTVQRILATEGDMELDEAGDVIGVLRDQ- QRYHEDIFGLTLRTQEVTSRIRTQSFSLQERQ LRG- AVPWAFDPPGSDTNSP SEQ ID NO: 9: Rev-Erbα
MTTLDSNNNTGGVITYIGSSGSSPSRTSPES- LYSDNSNGSFQSLTQGCPTYFPPSPTGSLTQ DPAR- SFGSIPPSLSDDGSPSSSSSSSSSSSFYNGSPPGSLQ- VAMEDSSRVSPSKSTSNITKL NGMVLLCKVCG- DVASGFHYGVHACEGCKGFFRRSIQQNIQYKRCLK- NENCSIVRINRN RCQQCRFKKCLSVGMSRDAVRFG- RIPKREKQRMLAEMQSAMNLANNQLSSQCPLETSP TQHPTPGPMGPSPPPAPVPSPLVGFSQFPQQLTPPR- SPSPEPTVEDVISQVARAHREIFTYA HDKLGSSP- GNFNANHASGSPPATTPHRWENQGCPPAPNDNNT- LAAQRHNEALNGLRQA PSSYPPTWPPGAHH- SCHQSNSNGHRLCPTHVYAAPEGKAPANSPRQGNS- KNVLLACP MNMYPHGRSGRTVQEIWEDFSMSFT- PAVREVVEFAKHIPGFRDLSQHDQVTLLKAGTF EVLMVRFASLFNVKDQTVMFLSRTTYSLQEL- GAMGMGDLLSAMFDFSEKLNSLALTEE ELGLFTAVVLVSADRSGMENSASVEQLQETLLRAL- RALVLKNRPLETSRFTKLLLKLPD LRTLNNMHSE- KLLSFRVDAQ SEQ ID NO: 10: Rev-Erbβ
MEVNAGGVIAYISSSSSASSPASCHSEGSENS- FQSSSSSVPSSPNSSNSDTNGNPKNGDLA NIEGILKN- DRIDCSMKTSKSSAPGMTKSHSGVTKFSGM- VLLCKVCGDVASGFHYGVHA CEGCKGFFRRSIQQ- NIQYKKCLKNENCSIMRMNRNRCQQCRFK- KCLSVGMSRDAVRFG RIPKREKQRMLIEMQSA- MKTMMNSQFSGHLQNDTLVEHHEQTALPAQEQL- RPKPQLEQ ENIKSSSPPSSDFAKEEVIGMVTRA- HKDTFMYNQEQQENSAESMQPQRGERIPKNMEQY NLNHDHCGNGLSSHFPCSESQQHLNGQFKGRNIM-HYPNGHAICIANGHCMNFSNAYTQ RVCDRVPID-GFSQNENKNSYLCNTGGRMHLVCPMSKSPYVDP-HKSGHEIWEEFSMSFTP AVKEVVEFAKRIPGFRDLS-QHDQVNLLKAGTFEVLMVRFASLFDAKERTVT-FLSGKKYS VDDLHSMGAGDLLNSMFEFSEKLN-ALQLSDEEMSLFTAVVLVSADRSGIENVNSVEAL QETLIRALRTLIMKNHPNEASIFTKLLLKLPDLR-SLNNMHSEELLAFKVHP

What is claimed is:

1. A pharmaceutical composition for photodynamic therapy comprising an effective amount of at least one type of conjugate comprising a porphyrin,
wherein the porphyrin is protoporphyrin IX (PpIX), and a recombinant protein comprising a di-alpha chain of human globin having the sequence set forth in SEQ ID NO:1 and two beta chains of human globin, each beta chain having the sequence set forth in SEQ ID NO:2, and
a pharmaceutically acceptable excipient.

2. The pharmaceutical composition according to claim 1, wherein the recombinant proteins of human alpha and beta globin are is non-covalently associated with the porphyrin.

3. The pharmaceutical composition of claim 1, wherein a molar ratio of PpIX to the recombinant protein of human alpha and beta globin is in the range of 0.05 to 4.

4. A method of treating cancer, the method comprising administering an effective amount of a pharmaceutical composition to an area of a patient in need of treatment, and
irradiating the area in need of treatment to generate reactive oxygen species after administration of the pharmaceutical composition, thereby treating the cancer and wherein
the pharmaceutical composition comprises an effective amount of at least one type of conjugate comprising a porphyrin,
wherein the porphyrin is protoporphyrin IX (PpIX),
and a recombinant protein comprising a di-alpha chain of human globin having the sequence set forth in SEQ ID NO:1 and two beta chains of human globin, each beta chain having the sequence set forth in SEQ ID NO:2, and
a pharmaceutically acceptable excipient.

5. The method of claim 4, wherein the PpIX and the recombinant protein of human alpha and beta globin are non-covalently associated.

6. The method of claim 4, wherein the molar ratio of PpIX to the recombinant protein of human alpha and beta globin is in the range of 0.05 to 4.

7. A method of producing a pharmaceutical composition, the method comprising
constructing a vector plasmid comprising a promoter, a recombinant protein of human alpha and beta globin, and a selectable marker,
transforming a bacterial strain by inserting the plasmid therein, wherein the bacterial strain endogenously produces PpIX;
selecting bacterial clones using an antibiotic corresponding to the selectable marker;
culturing the bacterial clones in a fermentation medium;
purifying conjugates from the fermentation medium, wherein the conjugates comprise PpIX non-covalently associated with the recombinant protein of human alpha and beta globin;
optionally adding a pharmaceutically acceptable carrier to the purified conjugates, thereby forming the pharmaceutical composition, and
wherein the porphyrin is protoporphyrin IX (PpIX),
wherein the recombinant protein comprises a di-alpha chain of human globin having the sequence set forth in SEQ ID NO:1 and two beta chains of human globin, each beta chain having the sequence set forth in SEQ ID NO:2.

8. The method of claim 7, wherein the bacterial strain is an *E. coli* strain selected from the group consisting of Jm109(DE3), clear coli and BL21 (DE3).

9. The method of claim 7, wherein the purified conjugates comprising PpIX and the recombinant protein of human alpha and beta globin are present at a molar ratio in the range of 0.05 to 4.

10. A method of reducing the volume of a tumor in a subject, the method comprising:
administering an effective amount of a pharmaceutical composition to an area of the subject where the tumor is found, wherein the pharmaceutical composition comprises
at least one type of conjugate comprising a porphyrin and a recombinant protein of human alpha and beta globin; and
wherein the porphyrin is protoporphyrin IX (PpIX),
wherein the recombinant protein comprises a di-alpha chain of human globin having the sequence set forth in SEQ ID NO:1 and two beta chains of human globin, each beta chain having the sequence set forth in SEQ ID NO:2;
a pharmaceutically acceptable excipient; and
irradiating the area where the tumor is found to generate reactive oxygen species after administration of the pharmaceutical composition, thereby reducing the volume of the tumor in the area where of the subject where the tumor is found.

11. The method of claim 10, wherein the PpIX and the recombinant protein of human alpha and beta globin are non-covalently associated.

12. The method of claim 10, wherein the molar ratio of PpIX to the recombinant protein of human alpha and beta globin is in the range of 0.05 to 4.

13. The method of claim 10, wherein the conjugate is administered to the subject at a concentration of 200 to 400 mg/kg.

* * * * *

SEQUENCE LISTING

```
<160> NUMBER OF SEQ ID NOS: 10

<210> SEQ ID NO 1
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg Gly Met Leu
    130                 135                 140

Ser Pro Ala Asp Lys Thr Asn Val Lys Ala Ala Trp Gly Lys Val Gly
145                 150                 155                 160

Ala His Ala Gly Glu Tyr Gly Ala Glu Ala Leu Glu Arg Met Phe Leu
                165                 170                 175

Ser Phe Pro Thr Thr Lys Thr Tyr Phe Pro His Phe Asp Leu Ser His
            180                 185                 190

Gly Ser Ala Gln Val Lys Gly His Gly Lys Lys Val Ala Asp Ala Leu
        195                 200                 205

Thr Asn Ala Val Ala His Val Asp Asp Met Pro Asn Ala Leu Ser Ala
    210                 215                 220

Leu Ser Asp Leu His Ala His Lys Leu Arg Val Asp Pro Val Asn Phe
225                 230                 235                 240

Lys Leu Leu Ser His Cys Leu Leu Val Thr Leu Ala Ala His Leu Pro
                245                 250                 255

Ala Glu Phe Thr Pro Ala Val His Ala Ser Leu Asp Lys Phe Leu Ala
            260                 265                 270

Ser Val Ser Thr Val Leu Thr Ser Lys Tyr Arg
        275                 280

<210> SEQ ID NO 2
<211> LENGTH: 146
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 2

Met His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 3
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Gly Leu Ser Asp Gly Glu Trp Gln Leu Val Leu Asn Val Trp Gly
1               5                   10                  15

Lys Val Glu Ala Asp Ile Pro Gly His Gly Gln Glu Val Leu Ile Arg
            20                  25                  30

Leu Phe Lys Gly His Pro Glu Thr Leu Glu Lys Phe Asp Lys Phe Lys
        35                  40                  45

His Leu Lys Ser Glu Asp Glu Met Lys Ala Ser Glu Asp Leu Lys Lys
    50                  55                  60

His Gly Ala Thr Val Leu Thr Ala Leu Gly Gly Ile Leu Lys Lys Lys
65                  70                  75                  80

Gly His His Glu Ala Glu Ile Lys Pro Leu Ala Gln Ser His Ala Thr
                85                  90                  95

Lys His Lys Ile Pro Val Lys Tyr Leu Glu Phe Ile Ser Glu Cys Ile
            100                 105                 110

Ile Gln Val Leu Gln Ser Lys His Pro Gly Asp Phe Gly Ala Asp Ala
        115                 120                 125

Gln Gly Ala Met Asn Lys Ala Leu Glu Leu Phe Arg Lys Asp Met Ala
    130                 135                 140

Ser Asn Tyr Lys Glu Leu Gly Phe Gln Gly
145                 150

```
<210> SEQ ID NO 4
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

Met Ile Asn Met Gly Asp Ser His Val Asp Thr Ser Ser Thr Val Ser
1               5                   10                  15

Glu Ala Val Ala Glu Val Ser Leu Phe Ser Met Thr Asp Met Ile
            20                  25                  30

Leu Phe Ser Leu Ile Val Gly Leu Leu Thr Tyr Trp Phe Leu Phe Arg
            35                  40                  45

Lys Lys Lys Glu Glu Val Pro Glu Phe Thr Lys Ile Gln Thr Leu Thr
50                  55                  60

Ser Ser Val Arg Glu Ser Ser Phe Val Glu Lys Met Lys Lys Thr Gly
65                  70                  75                  80

Arg Asn Ile Ile Val Phe Tyr Gly Ser Gln Thr Gly Thr Ala Glu Glu
                85                  90                  95

Phe Ala Asn Arg Leu Ser Lys Asp Ala His Arg Tyr Gly Met Arg Gly
            100                 105                 110

Met Ser Ala Asp Pro Glu Glu Tyr Asp Leu Ala Asp Leu Ser Ser Leu
            115                 120                 125

Pro Glu Ile Asp Asn Ala Leu Val Val Phe Cys Met Ala Thr Tyr Gly
130                 135                 140

Glu Gly Asp Pro Thr Asp Asn Ala Gln Asp Phe Tyr Asp Trp Leu Gln
145                 150                 155                 160

Glu Thr Asp Val Asp Leu Ser Gly Val Lys Phe Ala Val Phe Gly Leu
                165                 170                 175

Gly Asn Lys Thr Tyr Glu His Phe Asn Ala Met Gly Lys Tyr Val Asp
            180                 185                 190

Lys Arg Leu Glu Gln Leu Gly Ala Gln Arg Ile Phe Glu Leu Gly Leu
            195                 200                 205

Gly Asp Asp Asp Gly Asn Leu Glu Glu Asp Phe Ile Thr Trp Arg Glu
210                 215                 220

Gln Phe Trp Pro Ala Val Cys Glu His Phe Gly Val Glu Ala Thr Gly
225                 230                 235                 240

Glu Glu Ser Ser Ile Arg Gln Tyr Glu Leu Val Val His Thr Asp Ile
                245                 250                 255

Asp Ala Ala Lys Val Tyr Met Gly Glu Met Gly Arg Leu Lys Ser Tyr
            260                 265                 270

Glu Asn Gln Lys Pro Pro Phe Asp Ala Lys Asn Pro Phe Leu Ala Ala
            275                 280                 285

Val Thr Thr Asn Arg Lys Leu Asn Gln Gly Thr Glu Arg His Leu Met
290                 295                 300

His Leu Glu Leu Asp Ile Ser Asp Ser Lys Ile Arg Tyr Glu Ser Gly
305                 310                 315                 320

Asp His Val Ala Val Tyr Pro Ala Asn Asp Ser Ala Leu Val Asn Gln
                325                 330                 335

Leu Gly Lys Ile Leu Gly Ala Asp Leu Asp Val Val Met Ser Leu Asn
            340                 345                 350

Asn Leu Asp Glu Glu Ser Asn Lys Lys His Pro Phe Pro Cys Pro Thr
            355                 360                 365

```
Ser Tyr Arg Thr Ala Leu Thr Tyr Tyr Leu Asp Ile Thr Asn Pro Pro
    370                 375                 380

Arg Thr Asn Val Leu Tyr Glu Leu Ala Gln Tyr Ala Ser Glu Pro Ser
385                 390                 395                 400

Glu Gln Glu Leu Leu Arg Lys Met Ala Ser Ser Gly Glu Gly Lys
                405                 410                 415

Glu Leu Tyr Leu Ser Trp Val Val Glu Ala Arg Arg His Ile Leu Ala
            420                 425                 430

Ile Leu Gln Asp Cys Pro Ser Leu Arg Pro Pro Ile Asp His Leu Cys
        435                 440                 445

Glu Leu Leu Pro Arg Leu Gln Ala Arg Tyr Tyr Ser Ile Ala Ser Ser
450                 455                 460

Ser Lys Val His Pro Asn Ser Val His Ile Cys Ala Val Val Val Glu
465                 470                 475                 480

Tyr Glu Thr Lys Ala Gly Arg Ile Asn Lys Gly Val Ala Thr Asn Trp
            485                 490                 495

Leu Arg Ala Lys Glu Pro Ala Gly Glu Asn Gly Gly Arg Ala Leu Val
                500                 505                 510

Pro Met Phe Val Arg Lys Ser Gln Phe Arg Leu Pro Phe Lys Ala Thr
            515                 520                 525

Thr Pro Val Ile Met Val Gly Pro Gly Thr Gly Val Ala Pro Phe Ile
530                 535                 540

Gly Phe Ile Gln Glu Arg Ala Trp Leu Arg Gln Gln Gly Lys Glu Val
545                 550                 555                 560

Gly Glu Thr Leu Leu Tyr Tyr Gly Cys Arg Arg Ser Asp Glu Asp Tyr
            565                 570                 575

Leu Tyr Arg Glu Glu Leu Ala Gln Phe His Arg Asp Gly Ala Leu Thr
        580                 585                 590

Gln Leu Asn Val Ala Phe Ser Arg Glu Gln Ser His Lys Val Tyr Val
    595                 600                 605

Gln His Leu Leu Lys Gln Asp Arg Glu His Leu Trp Lys Leu Ile Glu
610                 615                 620

Gly Gly Ala His Ile Tyr Val Cys Gly Asp Ala Arg Asn Met Ala Arg
625                 630                 635                 640

Asp Val Gln Asn Thr Phe Tyr Asp Ile Val Ala Glu Leu Gly Ala Met
            645                 650                 655

Glu His Ala Gln Ala Val Asp Tyr Ile Lys Lys Leu Met Thr Lys Gly
        660                 665                 670

Arg Tyr Ser Leu Asp Val Trp Ser
    675                 680

<210> SEQ ID NO 5
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Asp Val Glu Lys Gly Lys Lys Ile Phe Ile Met Lys Cys Ser
1               5                   10                  15

Gln Cys His Thr Val Glu Lys Gly Gly Lys His Lys Thr Gly Pro Asn
            20                  25                  30

Leu His Gly Leu Phe Gly Arg Lys Thr Gly Gln Ala Pro Gly Tyr Ser
        35                  40                  45
```

```
Tyr Thr Ala Ala Asn Lys Asn Lys Gly Ile Ile Trp Gly Glu Asp Thr
            50                  55                  60

Leu Met Glu Tyr Leu Glu Asn Pro Lys Lys Tyr Ile Pro Gly Thr Lys
 65                  70                  75                  80

Met Ile Phe Val Gly Ile Lys Lys Glu Glu Arg Ala Asp Leu Ile
                    85                  90                  95

Ala Tyr Leu Lys Lys Ala Thr Asn Glu
                100                 105

<210> SEQ ID NO 6
<211> LENGTH: 1434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Asp His Met Phe Gly Val Gln Gln Ile Gln Pro Asn Val Ile
 1               5                  10                  15

Ser Val Arg Leu Phe Lys Arg Lys Val Gly Gly Leu Gly Phe Leu Val
                20                  25                  30

Lys Glu Arg Val Ser Lys Pro Pro Val Ile Ile Ser Asp Leu Ile Arg
            35                  40                  45

Gly Gly Ala Ala Glu Gln Ser Gly Leu Ile Gln Ala Gly Asp Ile Ile
        50                  55                  60

Leu Ala Val Asn Gly Arg Pro Leu Val Asp Leu Ser Tyr Asp Ser Ala
 65                  70                  75                  80

Leu Glu Val Leu Arg Gly Ile Ala Ser Glu Thr His Val Val Leu Ile
                85                  90                  95

Leu Arg Gly Pro Glu Gly Phe Thr Thr His Leu Glu Thr Thr Phe Thr
                100                 105                 110

Gly Asp Gly Thr Pro Lys Thr Ile Arg Val Thr Gln Pro Leu Gly Pro
            115                 120                 125

Pro Thr Lys Ala Val Asp Leu Ser His Gln Pro Pro Ala Gly Lys Glu
        130                 135                 140

Gln Pro Leu Ala Val Asp Gly Ala Ser Gly Pro Gly Asn Gly Pro Gln
145                 150                 155                 160

His Ala Tyr Asp Asp Gly Gln Glu Ala Gly Ser Leu Pro His Ala Asn
                165                 170                 175

Gly Leu Ala Pro Arg Pro Pro Gly Gln Asp Pro Ala Lys Lys Ala Thr
                180                 185                 190

Arg Val Ser Leu Gln Gly Arg Gly Glu Asn Asn Glu Leu Leu Lys Glu
            195                 200                 205

Ile Glu Pro Val Leu Ser Leu Leu Thr Ser Gly Ser Arg Gly Val Lys
        210                 215                 220

Gly Gly Ala Pro Ala Lys Ala Glu Met Lys Asp Met Gly Ile Gln Val
225                 230                 235                 240

Asp Arg Asp Leu Asp Gly Lys Ser His Lys Pro Leu Pro Leu Gly Val
                245                 250                 255

Glu Asn Asp Arg Val Phe Asn Asp Leu Trp Gly Lys Gly Asn Val Pro
                260                 265                 270

Val Val Leu Asn Asn Pro Tyr Ser Glu Lys Glu Gln Pro Pro Thr Ser
            275                 280                 285

Gly Lys Gln Ser Pro Thr Lys Asn Gly Ser Pro Ser Lys Cys Pro Arg
```

```
            290                 295                 300

Phe Leu Lys Val Lys Asn Trp Glu Thr Glu Val Val Leu Thr Asp Thr
    305                 310                 315                 320

Leu His Leu Lys Ser Thr Leu Glu Thr Gly Cys Thr Glu Tyr Ile Cys
                        325                 330                 335

Met Gly Ser Ile Met His Pro Ser Gln His Ala Arg Arg Pro Glu Asp
                        340                 345                 350

Val Arg Thr Lys Gly Gln Leu Phe Pro Leu Ala Lys Glu Phe Ile Asp
                    355                 360                 365

Gln Tyr Tyr Ser Ser Ile Lys Arg Phe Gly Ser Lys Ala His Met Glu
                370                 375                 380

Arg Leu Glu Glu Val Asn Lys Glu Ile Asp Thr Thr Ser Thr Tyr Gln
    385                 390                 395                 400

Leu Lys Asp Thr Glu Leu Ile Tyr Gly Ala Lys His Ala Trp Arg Asn
                        405                 410                 415

Ala Ser Arg Cys Val Gly Arg Ile Gln Trp Ser Lys Leu Gln Val Phe
                    420                 425                 430

Asp Ala Arg Asp Cys Thr Thr Ala His Gly Met Phe Asn Tyr Ile Cys
                435                 440                 445

Asn His Val Lys Tyr Ala Thr Asn Lys Gly Asn Leu Arg Ser Ala Ile
        450                 455                 460

Thr Ile Phe Pro Gln Arg Thr Asp Gly Lys His Asp Phe Arg Val Trp
    465                 470                 475                 480

Asn Ser Gln Leu Ile Arg Tyr Ala Gly Tyr Lys Gln Pro Asp Gly Ser
                        485                 490                 495

Thr Leu Gly Asp Pro Ala Asn Val Gln Phe Thr Glu Ile Cys Ile Gln
                    500                 505                 510

Gln Gly Trp Lys Pro Pro Arg Gly Arg Phe Asp Val Leu Pro Leu Leu
                515                 520                 525

Leu Gln Ala Asn Gly Asn Asp Pro Glu Leu Phe Gln Ile Pro Pro Glu
        530                 535                 540

Leu Val Leu Glu Val Pro Ile Arg His Pro Lys Phe Glu Trp Phe Lys
    545                 550                 555                 560

Asp Leu Gly Leu Lys Trp Tyr Gly Leu Pro Ala Val Ser Asn Met Leu
                        565                 570                 575

Leu Glu Ile Gly Gly Leu Glu Phe Ser Ala Cys Pro Phe Ser Gly Trp
                    580                 585                 590

Tyr Met Gly Thr Glu Ile Gly Val Arg Asp Tyr Cys Asp Asn Ser Arg
                595                 600                 605

Tyr Asn Ile Leu Glu Glu Val Ala Lys Lys Met Asn Leu Asp Met Arg
        610                 615                 620

Lys Thr Ser Ser Leu Trp Lys Asp Gln Ala Leu Val Glu Ile Asn Ile
    625                 630                 635                 640

Ala Val Leu Tyr Ser Phe Gln Ser Asp Lys Val Thr Ile Val Asp His
                        645                 650                 655

His Ser Ala Thr Glu Ser Phe Ile Lys His Met Glu Asn Glu Tyr Arg
                    660                 665                 670

Cys Arg Gly Gly Cys Pro Ala Asp Trp Val Trp Ile Val Pro Pro Met
                675                 680                 685

Ser Gly Ser Ile Thr Pro Val Phe His Gln Glu Met Leu Asn Tyr Arg
        690                 695                 700

Leu Thr Pro Ser Phe Glu Tyr Gln Pro Asp Pro Trp Asn Thr His Val
    705                 710                 715                 720
```

```
Trp Lys Gly Thr Asn Gly Thr Pro Thr Lys Arg Arg Ala Ile Gly Phe
            725                 730                 735

Lys Lys Leu Ala Glu Ala Val Lys Phe Ser Ala Lys Leu Met Gly Gln
            740                 745                 750

Ala Met Ala Lys Arg Val Lys Ala Thr Ile Leu Tyr Ala Thr Glu Thr
            755                 760                 765

Gly Lys Ser Gln Ala Tyr Ala Lys Thr Leu Cys Glu Ile Phe Lys His
        770                 775                 780

Ala Phe Asp Ala Lys Val Met Ser Met Glu Glu Tyr Asp Ile Val His
785                 790                 795                 800

Leu Glu His Glu Thr Leu Val Leu Val Val Thr Ser Thr Phe Gly Asn
                805                 810                 815

Gly Asp Pro Pro Glu Asn Gly Glu Lys Phe Gly Cys Ala Leu Met Glu
            820                 825                 830

Met Arg His Pro Asn Ser Val Gln Glu Glu Arg Lys Ser Tyr Lys Val
            835                 840                 845

Arg Phe Asn Ser Val Ser Ser Tyr Ser Asp Ser Gln Lys Ser Ser Gly
        850                 855                 860

Asp Gly Pro Asp Leu Arg Asp Asn Phe Glu Ser Ala Gly Pro Leu Ala
865                 870                 875                 880

Asn Val Arg Phe Ser Val Phe Gly Leu Gly Ser Arg Ala Tyr Pro His
                885                 890                 895

Phe Cys Ala Phe Gly His Ala Val Asp Thr Leu Leu Glu Glu Leu Gly
            900                 905                 910

Gly Glu Arg Ile Leu Lys Met Arg Glu Gly Asp Glu Leu Cys Gly Gln
            915                 920                 925

Glu Glu Ala Phe Arg Thr Trp Ala Lys Lys Val Phe Lys Ala Ala Cys
        930                 935                 940

Asp Val Phe Cys Val Gly Asp Asp Val Asn Ile Glu Lys Ala Asn Asn
945                 950                 955                 960

Ser Leu Ile Ser Asn Asp Arg Ser Trp Lys Arg Asn Lys Phe Arg Leu
                965                 970                 975

Thr Phe Val Ala Glu Ala Pro Glu Leu Thr Gln Gly Leu Ser Asn Val
            980                 985                 990

His Lys Lys Arg Val Ser Ala Ala  Arg Leu Leu Ser Arg  Gln Asn Leu
            995                 1000                1005

Gln Ser  Pro Lys Ser Ser  Arg Ser Thr Ile Phe Val  Arg Leu His
    1010                1015                1020

Thr Asn  Gly Ser Gln Glu Leu  Gln Tyr Gln Pro Gly  Asp His Leu
    1025                1030                1035

Gly Val  Phe Pro Gly Asn His  Glu Asp Leu Val Asn  Ala Leu Ile
    1040                1045                1050

Glu Arg  Leu Glu Asp Ala Pro  Pro Val Asn Gln Met  Val Lys Val
    1055                1060                1065

Glu Leu  Leu Glu Glu Arg Asn  Thr Ala Leu Gly Val  Ile Ser Asn
    1070                1075                1080

Trp Thr  Asp Glu Leu Arg Leu  Pro Pro Cys Thr Ile  Phe Gln Ala
    1085                1090                1095

Phe Lys  Tyr Tyr Leu Asp Ile  Thr Thr Pro Pro Thr  Pro Leu Gln
    1100                1105                1110

Leu Gln  Gln Phe Ala Ser Leu  Ala Thr Ser Glu Lys  Glu Lys Gln
    1115                1120                1125
```

```
Arg Leu Leu Val Leu Ser Lys Gly Leu Gln Glu Tyr Glu Glu Trp
    1130                1135                1140

Lys Trp Gly Lys Asn Pro Thr Ile Val Glu Val Leu Glu Glu Phe
    1145                1150                1155

Pro Ser Ile Gln Met Pro Ala Thr Leu Leu Thr Gln Leu Ser
    1160                1165                1170

Leu Leu Gln Pro Arg Tyr Tyr Ser Ile Ser Ser Pro Asp Met
    1175                1180                1185

Tyr Pro Asp Glu Val His Leu Thr Val Ala Ile Val Ser Tyr Arg
    1190                1195                1200

Thr Arg Asp Gly Glu Gly Pro Ile His His Gly Val Cys Ser Ser
    1205                1210                1215

Trp Leu Asn Arg Ile Gln Ala Asp Glu Leu Val Pro Cys Phe Val
    1220                1225                1230

Arg Gly Ala Pro Ser Phe His Leu Pro Arg Asn Pro Gln Val Pro
    1235                1240                1245

Cys Ile Leu Val Gly Pro Gly Thr Gly Ile Ala Pro Phe Arg Ser
    1250                1255                1260

Phe Trp Gln Gln Arg Gln Phe Asp Ile Gln His Lys Gly Met Asn
    1265                1270                1275

Pro Cys Pro Met Val Leu Val Phe Gly Cys Arg Gln Ser Lys Ile
    1280                1285                1290

Asp His Ile Tyr Arg Glu Glu Thr Leu Gln Ala Lys Asn Lys Gly
    1295                1300                1305

Val Phe Arg Glu Leu Tyr Thr Ala Tyr Ser Arg Glu Pro Asp Lys
    1310                1315                1320

Pro Lys Lys Tyr Val Gln Asp Ile Leu Gln Glu Gln Leu Ala Glu
    1325                1330                1335

Ser Val Tyr Arg Ala Leu Lys Glu Gln Gly Gly His Ile Tyr Val
    1340                1345                1350

Cys Gly Asp Val Thr Met Ala Ala Asp Val Leu Lys Ala Ile Gln
    1355                1360                1365

Arg Ile Met Thr Gln Gln Gly Lys Leu Ser Ala Glu Asp Ala Gly
    1370                1375                1380

Val Phe Ile Ser Arg Met Arg Asp Asp Asn Arg Tyr His Glu Asp
    1385                1390                1395

Ile Phe Gly Val Thr Leu Arg Thr Tyr Glu Val Thr Asn Arg Leu
    1400                1405                1410

Arg Ser Glu Ser Ile Ala Phe Ile Glu Glu Ser Lys Lys Asp Thr
    1415                1420                1425

Asp Glu Val Phe Ser Ser
    1430
```

<210> SEQ ID NO 7
<211> LENGTH: 1153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Ala Cys Pro Trp Lys Phe Leu Phe Lys Thr Lys Phe His Gln Tyr
1               5                   10                  15

Ala Met Asn Gly Glu Lys Asp Ile Asn Asn Val Glu Lys Ala Pro
            20                  25                  30
```

```
Cys Ala Thr Ser Ser Pro Val Thr Gln Asp Asp Leu Gln Tyr His Asn
             35                  40                  45
Leu Ser Lys Gln Gln Asn Glu Ser Pro Gln Pro Leu Val Glu Thr Gly
 50                  55                  60
Lys Lys Ser Pro Glu Ser Leu Val Lys Leu Asp Ala Thr Pro Leu Ser
 65                  70                  75                  80
Ser Pro Arg His Val Arg Ile Lys Asn Trp Gly Ser Gly Met Thr Phe
             85                  90                  95
Gln Asp Thr Leu His His Lys Ala Lys Gly Ile Leu Thr Cys Arg Ser
            100                 105                 110
Lys Ser Cys Leu Gly Ser Ile Met Thr Pro Lys Ser Leu Thr Arg Gly
            115                 120                 125
Pro Arg Asp Lys Pro Thr Pro Pro Asp Glu Leu Leu Pro Gln Ala Ile
            130                 135                 140
Glu Phe Val Asn Gln Tyr Tyr Gly Ser Phe Lys Glu Ala Lys Ile Glu
145                 150                 155                 160
Glu His Leu Ala Arg Val Glu Ala Val Thr Lys Glu Ile Glu Thr Thr
            165                 170                 175
Gly Thr Tyr Gln Leu Thr Gly Asp Glu Leu Ile Phe Ala Thr Lys Gln
            180                 185                 190
Ala Trp Arg Asn Ala Pro Arg Cys Ile Gly Arg Ile Gln Trp Ser Asn
            195                 200                 205
Leu Gln Val Phe Asp Ala Arg Ser Cys Ser Thr Ala Arg Glu Met Phe
210                 215                 220
Glu His Ile Cys Arg His Val Arg Tyr Ser Thr Asn Asn Gly Asn Ile
225                 230                 235                 240
Arg Ser Ala Ile Thr Val Phe Pro Gln Arg Ser Asp Gly Lys His Asp
            245                 250                 255
Phe Arg Val Trp Asn Ala Gln Leu Ile Arg Tyr Ala Gly Tyr Gln Met
            260                 265                 270
Pro Asp Gly Ser Ile Arg Gly Asp Pro Ala Asn Val Glu Phe Thr Gln
            275                 280                 285
Leu Cys Ile Asp Leu Gly Trp Lys Pro Lys Tyr Gly Arg Phe Asp Val
            290                 295                 300
Val Pro Leu Val Leu Gln Ala Asn Gly Arg Asp Pro Glu Leu Phe Glu
305                 310                 315                 320
Ile Pro Pro Asp Leu Val Leu Glu Val Ala Met Glu His Pro Lys Tyr
            325                 330                 335
Glu Trp Phe Arg Glu Leu Glu Leu Lys Trp Tyr Ala Leu Pro Ala Val
            340                 345                 350
Ala Asn Met Leu Leu Glu Val Gly Gly Leu Glu Phe Pro Gly Cys Pro
            355                 360                 365
Phe Asn Gly Trp Tyr Met Gly Thr Glu Ile Gly Val Arg Asp Phe Cys
            370                 375                 380
Asp Val Gln Arg Tyr Asn Ile Leu Glu Glu Val Gly Arg Arg Met Gly
385                 390                 395                 400
Leu Glu Thr His Lys Leu Ala Ser Leu Trp Lys Asp Gln Ala Val Val
            405                 410                 415
Glu Ile Asn Ile Ala Val Leu His Ser Phe Gln Lys Gln Asn Val Thr
            420                 425                 430
Ile Met Asp His His Ser Ala Ala Glu Ser Phe Met Lys Tyr Met Gln
            435                 440                 445
```

```
Asn Glu Tyr Arg Ser Arg Gly Gly Cys Pro Ala Asp Trp Ile Trp Leu
    450                 455                 460

Val Pro Pro Met Ser Gly Ser Ile Thr Pro Val Phe His Gln Glu Met
465                 470                 475                 480

Leu Asn Tyr Val Leu Ser Pro Phe Tyr Tyr Gln Val Glu Ala Trp
            485                 490                 495

Lys Thr His Val Trp Gln Asp Glu Lys Arg Pro Lys Arg Arg Glu
            500                 505                 510

Ile Pro Leu Lys Val Leu Val Lys Ala Val Leu Phe Ala Cys Met Leu
        515                 520                 525

Met Arg Lys Thr Met Ala Ser Arg Val Arg Val Thr Ile Leu Phe Ala
530                 535                 540

Thr Glu Thr Gly Lys Ser Glu Ala Leu Ala Trp Asp Leu Gly Ala Leu
545                 550                 555                 560

Phe Ser Cys Ala Phe Asn Pro Lys Val Cys Met Asp Lys Tyr Arg
                565                 570                 575

Leu Ser Cys Leu Glu Glu Glu Arg Leu Leu Val Val Thr Ser Thr
            580                 585                 590

Phe Gly Asn Gly Asp Cys Pro Gly Asn Gly Glu Lys Leu Lys Ser
            595                 600                 605

Leu Phe Met Leu Lys Glu Leu Asn Asn Lys Phe Arg Tyr Ala Val Phe
        610                 615                 620

Gly Leu Gly Ser Ser Met Tyr Pro Arg Phe Cys Ala Phe Ala His Asp
625                 630                 635                 640

Ile Asp Gln Lys Leu Ser His Leu Gly Ala Ser Gln Leu Thr Pro Met
                645                 650                 655

Gly Glu Gly Asp Glu Leu Ser Gly Gln Glu Asp Ala Phe Arg Ser Trp
            660                 665                 670

Ala Val Gln Thr Phe Lys Ala Ala Cys Glu Thr Phe Asp Val Arg Gly
            675                 680                 685

Lys Gln His Ile Gln Ile Pro Lys Leu Tyr Thr Ser Asn Val Thr Trp
        690                 695                 700

Asp Pro His His Tyr Arg Leu Val Gln Asp Ser Gln Pro Leu Asp Leu
705                 710                 715                 720

Ser Lys Ala Leu Ser Ser Met His Ala Lys Asn Val Phe Thr Met Arg
                725                 730                 735

Leu Lys Ser Arg Gln Asn Leu Gln Ser Pro Thr Ser Ser Arg Ala Thr
            740                 745                 750

Ile Leu Val Glu Leu Ser Cys Glu Asp Gly Gln Gly Leu Asn Tyr Leu
        755                 760                 765

Pro Gly Glu His Leu Gly Val Cys Pro Gly Asn Gln Pro Ala Leu Val
770                 775                 780

Gln Gly Ile Leu Glu Arg Val Val Asp Gly Pro Thr Pro His Gln Thr
785                 790                 795                 800

Val Arg Leu Glu Ala Leu Asp Glu Ser Gly Ser Tyr Trp Val Ser Asp
                805                 810                 815

Lys Arg Leu Pro Pro Cys Ser Leu Ser Gln Ala Leu Thr Tyr Phe Leu
            820                 825                 830

Asp Ile Thr Thr Pro Pro Thr Gln Leu Leu Leu Gln Lys Leu Ala Gln
            835                 840                 845

Val Ala Thr Glu Glu Pro Glu Arg Gln Arg Leu Glu Ala Leu Cys Gln
850                 855                 860

Pro Ser Glu Tyr Ser Lys Trp Lys Phe Thr Asn Ser Pro Thr Phe Leu
```

```
                865                 870                 875                 880
Glu Val Leu Glu Glu Phe Pro Ser Leu Arg Val Ser Ala Gly Phe Leu
                    885                 890                 895

Leu Ser Gln Leu Pro Ile Leu Lys Pro Arg Phe Tyr Ser Ile Ser Ser
            900                 905                 910

Ser Arg Asp His Thr Pro Thr Glu Ile His Leu Thr Val Ala Val Val
        915                 920                 925

Thr Tyr His Thr Arg Asp Gly Gln Gly Pro Leu His His Gly Val Cys
    930                 935                 940

Ser Thr Trp Leu Asn Ser Leu Lys Pro Gln Asp Pro Val Pro Cys Phe
945                 950                 955                 960

Val Arg Asn Ala Ser Gly Phe His Leu Pro Glu Asp Pro Ser His Pro
                965                 970                 975

Cys Ile Leu Ile Gly Pro Gly Thr Gly Ile Ala Pro Phe Arg Ser Phe
                    980                 985                 990

Trp Gln Gln Arg Leu His Asp Ser Gln His Lys Gly Val Arg Gly Gly
            995                 1000                1005

Arg Met Thr Leu Val Phe Gly Cys Arg Arg Pro Asp Glu Asp His
    1010                1015                1020

Ile Tyr Gln Glu Glu Met Leu Glu Met Ala Gln Lys Gly Val Leu
    1025                1030                1035

His Ala Val His Thr Ala Tyr Ser Arg Leu Pro Gly Lys Pro Lys
    1040                1045                1050

Val Tyr Val Gln Asp Ile Leu Arg Gln Gln Leu Ala Ser Glu Val
    1055                1060                1065

Leu Arg Val Leu His Lys Glu Pro Gly His Leu Tyr Val Cys Gly
    1070                1075                1080

Asp Val Arg Met Ala Arg Asp Val Ala His Thr Leu Lys Gln Leu
    1085                1090                1095

Val Ala Ala Lys Leu Lys Leu Asn Glu Glu Gln Val Glu Asp Tyr
    1100                1105                1110

Phe Phe Gln Leu Lys Ser Gln Lys Arg Tyr His Glu Asp Ile Phe
    1115                1120                1125

Gly Ala Val Phe Pro Tyr Glu Ala Lys Lys Asp Arg Val Ala Val
    1130                1135                1140

Gln Pro Ser Ser Leu Glu Met Ser Ala Leu
    1145                1150

<210> SEQ ID NO 8
<211> LENGTH: 1203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Asn Leu Lys Ser Val Ala Gln Glu Pro Gly Pro Pro Cys Gly
1               5                   10                  15

Leu Gly Leu Gly Leu Gly Leu Gly Leu Cys Gly Lys Gln Gly Pro Ala
                20                  25                  30

Thr Pro Ala Pro Glu Pro Ser Arg Ala Pro Ala Ser Leu Leu Pro Pro
            35                  40                  45

Ala Pro Glu His Ser Pro Pro Ser Ser Pro Leu Thr Gln Pro Pro Glu
        50                  55                  60
```

```
Gly Pro Lys Phe Pro Arg Val Lys Asn Trp Glu Val Gly Ser Ile Thr
 65                  70                  75                  80

Tyr Asp Thr Leu Ser Ala Gln Ala Gln Asp Gly Pro Cys Thr Pro
             85                  90                  95

Arg Arg Cys Leu Gly Ser Leu Val Phe Pro Arg Lys Leu Gln Gly Arg
            100                 105                 110

Pro Ser Pro Gly Pro Pro Ala Pro Glu Gln Leu Leu Ser Gln Ala Arg
            115                 120                 125

Asp Phe Ile Asn Gln Tyr Tyr Ser Ser Ile Lys Arg Ser Gly Ser Gln
            130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
                180                 185                 190

Leu Gln Val Phe Asp Ala Arg Asp Cys Arg Ser Ala Gln Glu Met Phe
                195                 200                 205

Thr Tyr Ile Cys Asn His Ile Lys Tyr Ala Thr Asn Arg Gly Asn Leu
                210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
                260                 265                 270

Leu Cys Ile Gln His Gly Trp Thr Pro Gly Asn Gly Arg Phe Asp Val
                275                 280                 285

Leu Pro Leu Leu Leu Gln Ala Pro Asp Asp Pro Pro Glu Leu Phe Leu
                290                 295                 300

Leu Pro Pro Glu Leu Val Leu Glu Val Pro Leu Glu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
                340                 345                 350

Phe Ser Gly Trp Tyr Met Ser Thr Glu Ile Gly Thr Arg Asn Leu Cys
                355                 360                 365

Asp Pro His Arg Tyr Asn Ile Leu Glu Asp Val Ala Val Cys Met Asp
            370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
            435                 440                 445

Val Pro Pro Ile Ser Gly Ser Leu Thr Pro Val Phe His Gln Glu Met
            450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
```

-continued

```
                485                 490                 495
Lys Glu Val Ala Asn Ala Val Lys Ile Ser Ala Ser Leu Met Gly Thr
                    500                 505                 510

Val Met Ala Lys Arg Val Lys Ala Thr Ile Leu Tyr Gly Ser Glu Thr
            515                 520                 525

Gly Arg Ala Gln Ser Tyr Ala Gln Gln Leu Gly Arg Leu Phe Arg Lys
        530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
    610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685

Cys Gly Gln Glu Glu Ala Phe Arg Gly Trp Ala Gln Ala Ala Phe Gln
690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
                725                 730                 735

Leu Ser Ala Gln Ala Glu Gly Leu Gln Leu Leu Pro Gly Leu Ile His
            740                 745                 750

Val His Arg Arg Lys Met Phe Gln Ala Thr Ile Arg Ser Val Glu Asn
        755                 760                 765

Leu Gln Ser Ser Lys Ser Thr Arg Ala Thr Ile Leu Val Arg Leu Asp
    770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
            820                 825                 830

Glu Lys Gly Ser Pro Gly Gly Pro Pro Gly Trp Val Arg Asp Pro
        835                 840                 845

Arg Leu Pro Pro Cys Thr Leu Arg Gln Ala Leu Thr Phe Phe Leu Asp
    850                 855                 860

Ile Thr Ser Pro Pro Ser Pro Gln Leu Leu Arg Leu Leu Ser Thr Leu
865                 870                 875                 880

Ala Glu Glu Pro Arg Glu Gln Gln Glu Leu Glu Ala Leu Ser Gln Asp
                885                 890                 895

Pro Arg Arg Tyr Glu Glu Trp Lys Trp Phe Arg Cys Pro Thr Leu Leu
            900                 905                 910
```

```
Glu Val Leu Glu Gln Phe Pro Ser Val Ala Leu Pro Ala Pro Leu Leu
        915                 920                 925

Leu Thr Gln Leu Pro Leu Leu Gln Pro Arg Tyr Tyr Ser Val Ser Ser
930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
            965                 970                 975

Ser Thr Trp Leu Ser Gln Leu Lys Pro Gly Asp Pro Val Pro Cys Phe
        980                 985                 990

Ile Arg Gly Ala Pro Ser Phe Arg  Leu Pro Pro Asp Pro  Ser Leu Pro
        995                 1000                1005

Cys Ile  Leu Val Gly Pro Gly  Thr Gly Ile Ala Pro  Phe Arg Gly
        1010                1015                1020

Phe Trp  Gln Glu Arg Leu His  Asp Ile Glu Ser Lys  Gly Leu Gln
        1025                1030                1035

Pro Thr  Pro Met Thr Leu Val  Phe Gly Cys Arg Cys  Ser Gln Leu
        1040                1045                1050

Asp His  Leu Tyr Arg Asp Glu  Val Gln Asn Ala Gln  Gln Arg Gly
        1055                1060                1065

Val Phe  Gly Arg Val Leu Thr  Ala Phe Ser Arg Glu  Pro Asp Asn
        1070                1075                1080

Pro Lys  Thr Tyr Val Gln Asp  Ile Leu Arg Thr Glu  Leu Ala Ala
        1085                1090                1095

Glu Val  His Arg Val Leu Cys  Leu Glu Arg Gly His  Met Phe Val
        1100                1105                1110

Cys Gly  Asp Val Thr Met Ala  Thr Asn Val Leu Gln  Thr Val Gln
        1115                1120                1125

Arg Ile  Leu Ala Thr Glu Gly  Asp Met Glu Leu Asp  Glu Ala Gly
        1130                1135                1140

Asp Val  Ile Gly Val Leu Arg  Asp Gln Gln Arg Tyr  His Glu Asp
        1145                1150                1155

Ile Phe  Gly Leu Thr Leu Arg  Thr Gln Glu Val Thr  Ser Arg Ile
        1160                1165                1170

Arg Thr  Gln Ser Phe Ser Leu  Gln Glu Arg Gln Leu  Arg Gly Ala
        1175                1180                1185

Val Pro  Trp Ala Phe Asp Pro  Pro Gly Ser Asp Thr  Asn Ser Pro
        1190                1195                1200

<210> SEQ ID NO 9
<211> LENGTH: 614
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Thr Thr Leu Asp Ser Asn Asn Thr Gly Gly Val Ile Thr Tyr
1               5                   10                  15

Ile Gly Ser Ser Gly Ser Ser Pro Ser Arg Thr Ser Pro Glu Ser Leu
                20                  25                  30

Tyr Ser Asp Asn Ser Asn Gly Ser Phe Gln Ser Leu Thr Gln Gly Cys
            35                  40                  45

Pro Thr Tyr Phe Pro Pro Ser Pro Thr Gly Ser Leu Thr Gln Asp Pro
```

```
                50                  55                  60
Ala Arg Ser Phe Gly Ser Ile Pro Pro Ser Leu Ser Asp Asp Gly Ser
 65                  70                  75                  80

Pro Ser Ser Ser Ser Ser Ser Ser Ser Ser Ser Ser Phe Tyr Asn
                 85                  90                  95

Gly Ser Pro Pro Gly Ser Leu Gln Val Ala Met Glu Asp Ser Ser Arg
                100                 105                 110

Val Ser Pro Ser Lys Ser Thr Ser Asn Ile Thr Lys Leu Asn Gly Met
                115                 120                 125

Val Leu Leu Cys Lys Val Cys Gly Asp Val Ala Ser Gly Phe His Tyr
                130                 135                 140

Gly Val His Ala Cys Glu Gly Cys Lys Gly Phe Phe Arg Arg Ser Ile
145                 150                 155                 160

Gln Gln Asn Ile Gln Tyr Lys Arg Cys Leu Lys Asn Glu Asn Cys Ser
                165                 170                 175

Ile Val Arg Ile Asn Arg Asn Arg Cys Gln Gln Cys Arg Phe Lys Lys
                180                 185                 190

Cys Leu Ser Val Gly Met Ser Arg Asp Ala Val Arg Phe Gly Arg Ile
                195                 200                 205

Pro Lys Arg Glu Lys Gln Arg Met Leu Ala Glu Met Gln Ser Ala Met
210                 215                 220

Asn Leu Ala Asn Asn Gln Leu Ser Ser Gln Cys Pro Leu Glu Thr Ser
225                 230                 235                 240

Pro Thr Gln His Pro Thr Pro Gly Pro Met Gly Pro Ser Pro Pro Pro
                245                 250                 255

Ala Pro Val Pro Ser Pro Leu Val Gly Phe Ser Gln Phe Pro Gln Gln
                260                 265                 270

Leu Thr Pro Pro Arg Ser Pro Ser Pro Glu Pro Thr Val Glu Asp Val
                275                 280                 285

Ile Ser Gln Val Ala Arg Ala His Arg Glu Ile Phe Thr Tyr Ala His
                290                 295                 300

Asp Lys Leu Gly Ser Ser Pro Gly Asn Phe Asn Ala Asn His Ala Ser
305                 310                 315                 320

Gly Ser Pro Pro Ala Thr Thr Pro His Arg Trp Glu Asn Gln Gly Cys
                325                 330                 335

Pro Pro Ala Pro Asn Asp Asn Asn Thr Leu Ala Ala Gln Arg His Asn
                340                 345                 350

Glu Ala Leu Asn Gly Leu Arg Gln Ala Pro Ser Ser Tyr Pro Pro Thr
                355                 360                 365

Trp Pro Pro Gly Pro Ala His His Ser Cys His Gln Ser Asn Ser Asn
                370                 375                 380

Gly His Arg Leu Cys Pro Thr His Val Tyr Ala Ala Pro Glu Gly Lys
385                 390                 395                 400

Ala Pro Ala Asn Ser Pro Arg Gln Gly Asn Ser Lys Asn Val Leu Leu
                405                 410                 415

Ala Cys Pro Met Asn Met Tyr Pro His Gly Arg Ser Gly Arg Thr Val
                420                 425                 430

Gln Glu Ile Trp Glu Asp Phe Ser Met Ser Phe Thr Pro Ala Val Arg
                435                 440                 445

Glu Val Val Glu Phe Ala Lys His Ile Pro Gly Phe Arg Asp Leu Ser
                450                 455                 460

Gln His Asp Gln Val Thr Leu Leu Lys Ala Gly Thr Phe Glu Val Leu
465                 470                 475                 480
```

```
Met Val Arg Phe Ala Ser Leu Phe Asn Val Lys Asp Gln Thr Val Met
            485                 490                 495

Phe Leu Ser Arg Thr Thr Tyr Ser Leu Gln Glu Leu Gly Ala Met Gly
            500                 505                 510

Met Gly Asp Leu Leu Ser Ala Met Phe Asp Phe Ser Glu Lys Leu Asn
            515                 520                 525

Ser Leu Ala Leu Thr Glu Glu Glu Leu Gly Leu Phe Thr Ala Val Val
            530                 535                 540

Leu Val Ser Ala Asp Arg Ser Gly Met Glu Asn Ser Ala Ser Val Glu
545                 550                 555                 560

Gln Leu Gln Glu Thr Leu Leu Arg Ala Leu Arg Ala Leu Val Leu Lys
                565                 570                 575

Asn Arg Pro Leu Glu Thr Ser Arg Phe Thr Lys Leu Leu Leu Lys Leu
            580                 585                 590

Pro Asp Leu Arg Thr Leu Asn Asn Met His Ser Glu Lys Leu Leu Ser
            595                 600                 605

Phe Arg Val Asp Ala Gln
    610

<210> SEQ ID NO 10
<211> LENGTH: 579
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Val Asn Ala Gly Gly Val Ile Ala Tyr Ile Ser Ser Ser Ser
1               5                   10                  15

Ser Ala Ser Ser Pro Ala Ser Cys His Ser Glu Gly Ser Glu Asn Ser
            20                  25                  30

Phe Gln Ser Ser Ser Ser Ser Val Pro Ser Ser Pro Asn Ser Ser Asn
            35                  40                  45

Ser Asp Thr Asn Gly Asn Pro Lys Asn Gly Asp Leu Ala Asn Ile Glu
50                  55                  60

Gly Ile Leu Lys Asn Asp Arg Ile Asp Cys Ser Met Lys Thr Ser Lys
65                  70                  75                  80

Ser Ser Ala Pro Gly Met Thr Lys Ser His Ser Gly Val Thr Lys Phe
                85                  90                  95

Ser Gly Met Val Leu Leu Cys Lys Val Cys Gly Asp Val Ala Ser Gly
            100                 105                 110

Phe His Tyr Gly Val His Ala Cys Glu Gly Cys Lys Gly Phe Phe Arg
            115                 120                 125

Arg Ser Ile Gln Gln Asn Ile Gln Tyr Lys Lys Cys Leu Lys Asn Glu
            130                 135                 140

Asn Cys Ser Ile Met Arg Met Asn Arg Asn Arg Cys Gln Gln Cys Arg
145                 150                 155                 160

Phe Lys Lys Cys Leu Ser Val Gly Met Ser Arg Asp Ala Val Arg Phe
                165                 170                 175

Gly Arg Ile Pro Lys Arg Glu Lys Gln Arg Met Leu Ile Glu Met Gln
            180                 185                 190

Ser Ala Met Lys Thr Met Met Asn Ser Gln Phe Ser Gly His Leu Gln
            195                 200                 205

Asn Asp Thr Leu Val Glu His His Glu Gln Thr Ala Leu Pro Ala Gln
```

-continued

```
                  210               215               220
Glu Gln Leu Arg Pro Lys Pro Gln Leu Glu Gln Glu Asn Ile Lys Ser
225                 230                 235                 240

Ser Ser Pro Pro Ser Ser Asp Phe Ala Lys Glu Glu Val Ile Gly Met
                245                 250                 255

Val Thr Arg Ala His Lys Asp Thr Phe Met Tyr Asn Gln Glu Gln Gln
                260                 265                 270

Glu Asn Ser Ala Glu Ser Met Gln Pro Gln Arg Gly Glu Arg Ile Pro
                275                 280                 285

Lys Asn Met Glu Gln Tyr Asn Leu Asn His Asp His Cys Gly Asn Gly
                290                 295                 300

Leu Ser Ser His Phe Pro Cys Ser Glu Ser Gln Gln His Leu Asn Gly
305                 310                 315                 320

Gln Phe Lys Gly Arg Asn Ile Met His Tyr Pro Asn Gly His Ala Ile
                325                 330                 335

Cys Ile Ala Asn Gly His Cys Met Asn Phe Ser Asn Ala Tyr Thr Gln
                340                 345                 350

Arg Val Cys Asp Arg Val Pro Ile Asp Gly Phe Ser Gln Asn Glu Asn
                355                 360                 365

Lys Asn Ser Tyr Leu Cys Asn Thr Gly Gly Arg Met His Leu Val Cys
                370                 375                 380

Pro Met Ser Lys Ser Pro Tyr Val Asp Pro His Lys Ser Gly His Glu
385                 390                 395                 400

Ile Trp Glu Glu Phe Ser Met Ser Phe Thr Pro Ala Val Lys Glu Val
                    405                 410                 415

Val Glu Phe Ala Lys Arg Ile Pro Gly Phe Arg Asp Leu Ser Gln His
                420                 425                 430

Asp Gln Val Asn Leu Leu Lys Ala Gly Thr Phe Glu Val Leu Met Val
                435                 440                 445

Arg Phe Ala Ser Leu Phe Asp Ala Lys Glu Arg Thr Val Thr Phe Leu
450                 455                 460

Ser Gly Lys Lys Tyr Ser Val Asp Asp Leu His Ser Met Gly Ala Gly
465                 470                 475                 480

Asp Leu Leu Asn Ser Met Phe Glu Phe Ser Glu Lys Leu Asn Ala Leu
                    485                 490                 495

Gln Leu Ser Asp Glu Glu Met Ser Leu Phe Thr Ala Val Val Leu Val
                500                 505                 510

Ser Ala Asp Arg Ser Gly Ile Glu Asn Val Asn Ser Val Glu Ala Leu
                515                 520                 525

Gln Glu Thr Leu Ile Arg Ala Leu Arg Thr Leu Ile Met Lys Asn His
                530                 535                 540

Pro Asn Glu Ala Ser Ile Phe Thr Lys Leu Leu Leu Lys Leu Pro Asp
545                 550                 555                 560

Leu Arg Ser Leu Asn Asn Met His Ser Glu Glu Leu Leu Ala Phe Lys
                    565                 570                 575

Val His Pro
```